United States Patent
Li et al.

(10) Patent No.: US 8,350,087 B2
(45) Date of Patent: Jan. 8, 2013

(54) BIODEGRADABLE THERMOGELLING POLYMER

(75) Inventors: Jun Li, Singapore (SG); Xian Jun Loh, Singapore (SG); Suat Hong Goh, Singapore (SG)

(73) Assignees: Agency for Science, Technology and Research, Singapore (SG); National University of Singapore, Singapore (SG)

( * ) Notice: Subject to any disclaimer, the term of this patent is extended or adjusted under 35 U.S.C. 154(b) by 609 days.

(21) Appl. No.: 12/296,923

(22) PCT Filed: Apr. 12, 2007

(86) PCT No.: PCT/SG2007/000097
§ 371 (c)(1),
(2), (4) Date: Oct. 10, 2008

(87) PCT Pub. No.: WO2007/117222
PCT Pub. Date: Oct. 18, 2007

(65) Prior Publication Data
US 2010/0080795 A1    Apr. 1, 2010

Related U.S. Application Data

(60) Provisional application No. 60/791,199, filed on Apr. 12, 2006.

(51) Int. Cl.
*C07C 213/00* (2006.01)
(52) U.S. Cl. ...... 564/505; 564/504; 514/44 R; 424/93.1; 525/418
(58) Field of Classification Search .......... 564/505, 564/504; 514/1.1, 44 R; 424/93.1; 525/418
See application file for complete search history.

(56) References Cited

U.S. PATENT DOCUMENTS

| | | | |
|---|---|---|---|
| 5,665,831 A | | 9/1997 | Neuenschwander |
| 6,156,852 A | * | 12/2000 | Asrar et al. ............ 525/450 |
| 6,284,838 B1 | * | 9/2001 | Silbiger ............ 525/54.4 |
| 2002/0041898 A1 | | 4/2002 | Unger |
| 2004/0147016 A1 | | 7/2004 | Rowley |
| 2004/0247624 A1 | | 12/2004 | Unger |
| 2005/0058688 A1 | | 3/2005 | Boerger |
| 2005/0112172 A1 | | 5/2005 | Pacetti |
| 2005/0147647 A1 | * | 7/2005 | Glauser et al. ............ 424/426 |
| 2005/0214339 A1 | | 9/2005 | Tang |
| 2005/0233062 A1 | * | 10/2005 | Hossainy et al. ............ 427/2.1 |
| 2005/0266038 A1 | | 12/2005 | Glauser |
| 2006/0178477 A1 | | 8/2006 | Neuenschwander |

FOREIGN PATENT DOCUMENTS

| | | |
|---|---|---|
| EP | 0696605 A1 | 2/1996 |
| EP | 1498147 A1 | 1/2003 |
| WO | WO 03/070292 A1 | 8/2003 |

(Continued)

OTHER PUBLICATIONS

Huang, K. et al., "Synthesis and Characterization of Self-Assembling Block Copolymers Containing Bioadhesive End Groups", Biomacromolecules, Mar. 2002, pp. 397-406, vol. 3, Issue 2.

(Continued)

*Primary Examiner* — Shane Fang
(74) *Attorney, Agent, or Firm* — Klarquist Sparkman, LLP

(57) ABSTRACT

There is provided a polymer comprising blocks of at least one polyethylene glycol) block, at least one poly(propylene glycol) block and at least one poly(hydroxybutyrate) block. Also provided is a method of making the polymer and a method of using the polymer.

26 Claims, 17 Drawing Sheets

FOREIGN PATENT DOCUMENTS

WO    WO 03/092468 A2    11/2003

OTHER PUBLICATIONS

Daga, A. et al., "Enhanced engraftment of EPO-transduced human bone marrow stromal cells transplanted in a 3D matrix in non-conditioned NOD/SCID mice", Gene Therapy, Jul. 2002, pp. 915-921, vol. 9, Issue 14.

Packhaeuser, C.B. et al., "In situ forming parenteral drug delivery systems: an overview", European Journal of Pharmaceutics and Biopharmaceutics, Sep. 2004, pp. 445-455, vol. 58, Issue 2.

Heller, J. et al., "Development and applications of injectable poly(ortho esters) for pain control and periodontal treatment", Biomaterials, Nov. 2002, pp. 4397-4404, vol. 23, Issue 22.

Hill-West, J.L. et al., "Inhibition of thrombosis and intimal thickening by in situ photopolymerization of thin hydrogel barriers", Proceedings of the National Academy of Sciences of the United States of America, 21, Jun. 1994, pp. 5967-5971, vol. 91, Issue 13.

Gilbert, J.C. et al., "Drug release from Pluronic F-127 gels", International Journal of Pharmaceutics, Oct. 1986, pp. 223-228, vol. 32, Issues 2-3.

Nalbandian, R. et al., "Artificial skin. II. Pluronic F-127 silver nitrate or silver lactate gel in the treatment of thermal burns", Journal of Biomedical Materials Research, Nov. 1972, pp. 583-590, vol. 6, Issue 6.

Exner, A.A. et al., "Enhancement of carboplatin toxicity by Pluronic block copolymers", Journal of Controlled Release, Aug. 18, 2005, pp. 188-197, vol. 106, Issues 1-2.

Esposito, E. et al., "Comparative analysis of tetracycline-containing dental gels: Poloxamer- and monoglyceride-based formulations", International Journal of Pharmaceutics, Sep. 27, 1996, pp. 9-23, vol. 142, Issue 1.

Katakam, M. et al., "Controlled release of human growth hormone following subcutaneous administration in dogs", International Journal of Pharmaceutics, Jun. 13, 1997, pp. 53-58, vol. 152, Issue 1.

Blonder, J.M. et al., "Dose-dependent hyperlipidemia in rabbits following administration of poloxamer 407 gel", Life Sciences, Oct. 15, 1999, pp. PL261-PL266, vol. 65, Issue 21.

Wout, Z.G.M. et al., Journal of Parenteral Science and Technology, 1992, vol. 46, pp. 192-200.

Palmer, W.K. et al., "Poloxamer 407-induced atherogenesis in the C57BL/6 mouse", Atherosclerosis, Jan. 1, 1998, pp. 115-123, vol. 136, Issue 1.

Ho, A.K. et al., Hydrophobic Domains in Thermogelling Solutions of Polyether- Modified Poly(Acrylic Acid), Langmuir, Apr. 16, 2002, pp. 3005-3013, vol. 18, Issue 8.

Cleary, J. et al., "Diffusion and Release of Solutes in Pluronic-g-poly(acrylic acid) Hydrogels", Langmuir, Oct. 28, 2003, pp. 9162-9172, vol. 19, Issue 22.

Bromberg, L., "Polyether-Modified Poly(acrylic acid): Synthesis and Applications", Industrial & Engineering Chemistry Research, Nov. 1998, pp. 4267-4274, vol. 37, Issue 11.

Bromberg, L., "Properties of Aqueous Solutions and Gels of Poly-(ethylene oxide)-b-poly(propylene oxide)-b-poly(ethylene oxide)-g-poly(acrylic acid)", The Journal of Physical Chemistry B, Dec. 24, 1998, pp. 10736-10744, vol. 102, Issue 52.

Ahn, J.S. et al., "Slow eroding biodegradable multiblock poloxamer copolymers", Polymer International, May 2005, pp. 842-847, vol. 54, Issue 5.

Cohn, D. et al., "Improved reverse thermo-responsive polymeric systems", Biomaterials, Sep. 2003, pp. 3707-3714, vol. 24, Issue 21.

Cohn, D. and Sosnik, A., "Reverse thermo-responsive poly(ethylene oxide) and poly(propylene oxide) multiblock copolymers", Biomaterials, Feb. 2005, pp. 349-357, vol. 26, Issue 4.

Hwang, M.J. et al., "Caprolactonic Poloxamer Analog: PEG-PCL-PEG", Biomacromolecules, Mar. 2005, pp. 885-890, vol. 6, Issue 2.

Jeong, B. et al., "Drug release from biodegradable injectable thermosensitive hydrogel of PEG-PLGA-PEG triblock copolymers", Journal of Controlled Release, Jan. 3, 2000, pp. 155-163, vol. 63, Issues 1-2.

Jeong, B. et al., "Biodegradable block copolymers as injectable drug-delivery systems", Nature, Aug. 28, 1997, pp. 860-862, vol. 388, No. 6645.

Li, J. et al., "Synthesis and Characterization of New Biodegradable Amphiphilic Poly(ethylene oxide)-b-poly[(R)-3-hydroxy butyrate]-b-poly(ethylene oxide) Triblock Copolymers", Macromolecules, Apr. 22, 2003, pp. 2661-2667, vol. 36, Issue 8.

Li, J. et al., Micellization Phenomena of Biodegradable Amphiphilic Triblock Copolymers Consisting of Poly(β-hydroxyalkanoic acid) and Poly(ethylene oxide), Langmuir, Sep. 13, 2005, pp. 8681-8685, vol. 21, Issue 19.

Li, X. et al., "Dynamic and Static Light Scattering Studies on Self-Aggregation Behavior of Biodegradable Amphiphilic Poly(ethylene oxide)-Poly[(R)-3-hydroxybutyrate]-Poly(ethylene oxide) Triblock Copolymers in Aqueous Solution", The Journal of Physical Chemistry B, Mar. 30, 2006, pp. 5920-5926, vol. 110, Issue 12.

Li, X. et al., "Poly(ester urethane)s Consisting of Poly[(R)-3-hydroxybutyrate] and Poly(ethylene glycol) as Candidate Biomaterials: Characterization and Mechanical Property Study", Biomacromolecules, Sep. 2005, pp. 2740-2747, vol. 6, Issue 5.

Loh, X.J. et al., "The in vitro hydrolysis of poly(ester urethane)s consisting of poly[(R)-3-hydroxybutyrate] and poly(ethylene glycol)", Biomaterials, Mar. 2006, pp. 1841-1850, vol. 27, Issue 9.

Loh, X.J., et al. Compositional study and cytotoxicity of biodegradable poly(ester urethane)s consisting of poly [(R))-3-hydroxybutyrate] and poly(ethylene glycol). Materials Science and Engineering C 27 (2007) 267-273.

Alexandridis, P. et al., "Micellization of Poly(ethylene oxide)-Poly(propylene oxide)-Poly(ethylene oxide) Triblock Copolymers in Aqueous Solutions: Thermodynamics of Copolymer Association", Macromolecules, Apr. 25, 1994, pp. 2414-2425, vol. 27, Issue 19.

Bae, S.J. et al., "Thermogelling Poly(caprolactone-b-caprolactone) Aqueous Solutions", Macromolecules, Jun. 14, 2005, pp. 5260-5265, vol. 38, Issue 12.

Jeong, B. et al., "Thermoreversible Gelation of PEG-PLGA-PEG Triblock Copolymer Aqueous Solutions", Macromolecules, Oct. 19, 1999, pp. 7064-7069, vol. 32, Issue 21.

Behravesh, E. et al., "Synthesis and Characterization of Triblock Copolymers of Methoxy Poly (ethylene glycol) and Poly(propylene fumarate)", Biomacromolecules, Jan. 2002, pp. 153-158, vol. 3, Issue 1.

Jeong, B. et al., "Biodegradable thermosensitive micelles of PEG-PLGA-PEG triblock copolymers", Colloids and Surfaces B: Biointerfaces, Nov. 1999, pp. 185-193, vol. 16, Issues 1-4.

Jeong, B. et al., "Phase Transition of the PLGA-g-PEG Copolymer Aqueous Solutions", The Journal of Physical Chemistry B, Sep. 18, 2003, pp. 10032-10039, vol. 107, Issue 37.

Lee, B. et al., "A Thermosensitive Poly(organophosphazene) Gel", Macromolecules, May 7, 2002, pp. 3876-3879, vol. 35, Issue 10.

Durand, A. et al., "Thermosensitive Graft Copolymers: NMR Investigation and Comparison with Rheological Behaviour", The Journal of Physical Chemistry B, Oct. 12, 2000, pp. 9371-9377, vol. 104, Issue 40.

Jeong, B. et al., "Thermogelling Biodegradable Polymers with Hydrophilic Backbones: PEG-g-PLGA", Macromolecules, Oct. 31, 2000, pp. 8317-8322, vol. 33, Issue 22.

Harris, J. M., Poly(ethylene glycol) Chemistry, Plenum Press: New York, 1992, pp. 263-268.

Harris J. and Zalipsky S. Poly(ethylene glycol) Chemistry and Biological Applications, 1997, pp. 16-30.

Booth, C. and Attwood, D., "Effects of block architecture and composition on the association properties of poly (oxyalkylene) copolymers in aqueous solution", Macromolecular Rapid Communications, Jun. 2000, pp. 501-527, vol. 21, Issue 9.

International Search Report and Written Opinion for PCT/SG2007/000097, 2007.

International Preliminary Report on Patentability for PCT/SG2007/000097, 2007.

\* cited by examiner

BIODEGRADABLE THERMOGELLING POLYMER

CROSS-REFERENCE TO RELATED APPLICATION

This application claims benefit and priority from U.S. provisional patent application No. 60/791,199, filed on Apr. 12, 2006, the contents of which are incorporated herein by reference.

FIELD OF THE INVENTION

The present invention relates generally to polymers, and particularly to biodegradable, thermogelling polymers.

BACKGROUND OF THE INVENTION

Polymer systems are being developed for various in vivo applications, including delivery vehicles for controlled release of drugs when implanted in a subject's body. Such systems are particularly useful for therapeutic biomolecules such as proteins or peptides, which tend to be very sensitive to degradation within the body. Polymer systems can be designed that exhibit altered properties in response to changes in environment, such as changes in temperature, pH and surrounding solution conditions.

In particular, the synthesis of thermogelling polymers has attracted much attention because of their suitability for applications such as drug delivery and tissue engineering (1-6). Bioactive agents can be incorporated in the solution state at low temperatures, which can then be injected in vivo where the higher body temperature induces formation of a gel depot. This depot can be used for the controlled release of the bioactive agents. Biodegradability of the polymers is advantageous, since degradation of the polymer into smaller fragments allows for subsequent removal of the polymer from the body. Low critical gelation concentration ("CGC") is also preferred, as lower concentrations of polymer can be used to create a gel, resulting in smaller amounts of polymer being implanted in a subject.

As an example of thermogelling polymers, Pluronics™ or Poloxamers™, the triblock copolymers of poly(ethylene glycol)-poly(propylene glycol)-poly(ethylene glycol) (PEG-PPG-PEG), have been widely investigated for controlled drug delivery (6, 7), wound covering (8), and chemosensitizing for cancer therapy (9). However, these polymers generally have a high CGC, typically 15-20 wt % or above, exhibit poor resilience, and tend to exhibit burst effect in the release of bioactive agents. These shortcomings have made this system unsuitable for many biomedical applications (10-11). Moreover, Pluronics™ copolymers are non-biodegradable and have been reported to induce hyperlipidemia and increase the plasma level of cholesterol in rabbits and rats, suggesting that its use in the human body may not be an attractive option (12-14).

Attempts have been made to lower the CGCs of a thermogelling copolymer containing Pluronics™. By grafting Pluronic™ to poly(acrylic acid), polymers having very low CGCs (0.1 wt %) have been synthesized (15-18). However, these polymers are non-biodegradable and clearance from the body could be difficult.

High molecular weight multi-block Pluronics™ with a short junction linkages have been synthesized and found to exhibit lower CGCs than Pluronics™ (19-20).

Cohn et al. have synthesized reverse thermogelling multi-block copolymers based on PEG, PPG and oligo-caprolactone (21). These biodegradable copolymers exhibited CGCs of 10 wt %; the incorporation of oligo-caprolactone segments lowered the CGCs of the copolymers as compared with the PPG/PEG multi-block copolymers. The viscosities of the gels were also lowered compared with the PPG/PEG multiblock copolymers.

Pluronic™ analogs were developed where the middle PPG block was replaced by a biodegradable polyester such as poly(ε-caprolactone) or poly(L-lactide). Although the CGCs of such polymers occur in a similar range compared to Pluronics™ (22), these polymers are more useful in biomedical applications because of their biodegradability.

Thus, there exists a need for a biodegradable, thermogelling polymer that exhibits a lower CGC compared to existing polymers such as Pluronics™.

SUMMARY OF THE INVENTION

There are presently provided novel polymers comprising blocks of poly(ethylene glycol) (PEG), poly(propylene glycol) (PPG) and poly(hydroxybutyrate) (PHB). The multi-block polymers are biocompatible, biodegradable, have thermogelling characteristics and have relatively low critical gelling concentrations, making them suitable for various in vivo applications, including as scaffolding, wound coverings and drug delivery vehicles. In particular, the novel polymers are suitable for formulation in injectable drug systems, which can be formulated at low temperatures and which form a gel depot in situ upon subcutaneous injection in a subject's body.

In one aspect, there is provided a polymer comprising blocks of at least one poly(ethylene glycol) block, at least one polypropylene glycol) block and at least one poly(hydroxybutyrate) block.

In another aspect, there is provided a composition comprising a polymer as described herein and a therapeutic agent.

In yet another aspect, there is provided a method of making a polymer comprising at least one poly(ethylene glycol) block, at least one poly(propylene glycol) block and at least one poly(hydroxybutyrate) block, the method comprising reacting poly(hydroxybutyrate)-diol, poly(ethylene glycol) and poly(propylene glycol) with a diisocyanate.

In yet another aspect, there is provided a method of delivering a therapeutic agent to a subject, the method comprising delivering a composition as described herein to the body of a subject.

In yet another aspect, there is provided use of a polymer as described herein for delivering a therapeutic agent to the body of a subject or use of a polymer as described herein in the manufacture of a medicament for delivering a therapeutic agent to the body of a subject.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1:
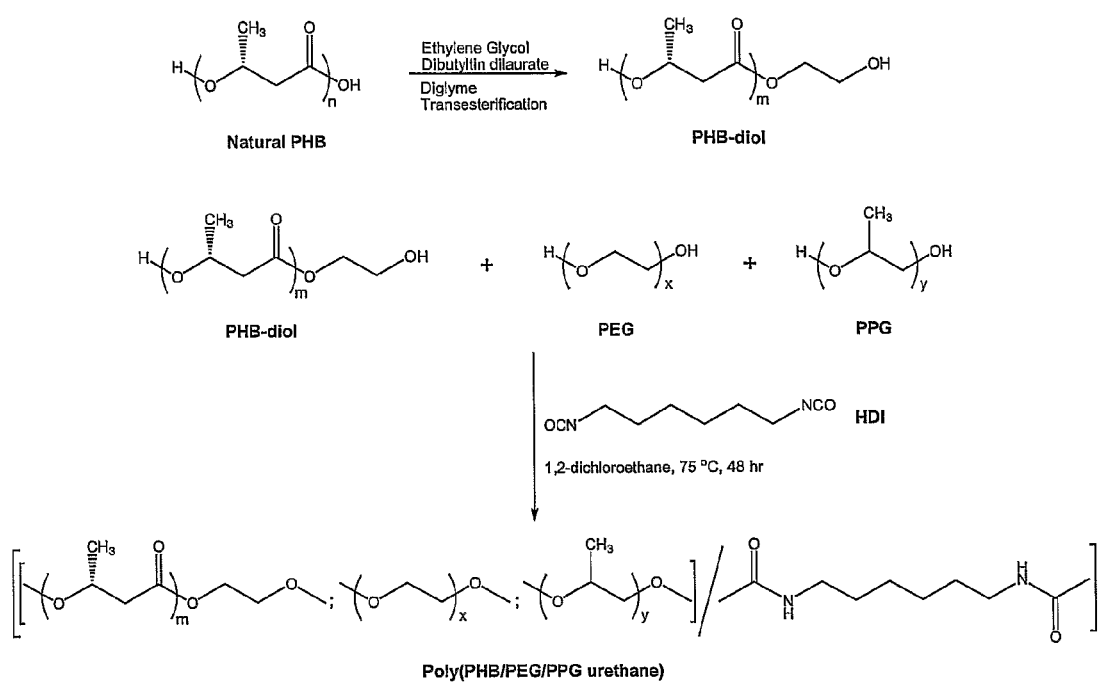
FIG. 1 is a schematic representation of a synthesis mechanism for PHB-diol and poly(PHB/PEG/PPG urethane)s.

In one aspect, there is presently provided a multiblock polymer comprising at least one block of PEG, at least one block of PPG and at least one block of PHB. The polymer contains hydrophilic blocks contributed by the PEG and the PPG and hydrophobic blocks contributed by the PHB.

The PEG and PPG blocks are biocompatible and clearance from the body is possible for blocks of lower molecular weight, for example about 10,000 g.mol$^{-1}$. PEG provides hydrophilic blocks that can absorb and retain large quantities of water, while PPG blocks are highly thermosensitive and provide a balanced hydrophobicity and hydrophilicity at different temperatures, facilitating the formation of a thermosensitive hydrogel.

PHB is a natural biopolyester that degrades to give 3-hydroxybutyric acid, which is a trace component in the human blood. PHB is highly crystalline and highly hydrophobic, showing a greater hydrophobicity than either poly(lactic acid) or poly(ε-caprolactone) (23). Incorporation of PHB blocks interspersed with PEG and PPG blocks allows for the formation of physical crosslinking in the hydrogel, increasing its resilience. Additionally, PHB blocks provide biodegradable segments at intervals along the polymer backbone, facilitating the degradation of the polymer into smaller fragments and subsequent removal of the polymer from the body.

The PEG blocks incorporated into the polymer may have a number average molecular weight ($M_n$) of about 10 000 g.mol$^{-1}$ or less, about 8 000 g.mol$^{-1}$ or less, about 5 000 g.mol$^{-1}$ or less, about 3 000 g.mol$^{-1}$ or less, about 2 000 g.mol$^{-1}$ or less, about 1 000 g.mol$^{-1}$ or less, about 800 g.mol$^{-1}$ or less, about 400 g.mol$^{-1}$ or less, or about 200 g.mol$^{-1}$ or less. In a particular embodiment, the PEG used has an $M_n$ of about 2 000 g.mol$^{-1}$ or less. PEGs of various sizes are commercially available and can readily be used in the present polymer.

The total amount of PEG in the polymer may be about 65 wt % or less, about 60 wt % or less, about 55 wt % or less, or about 50 wt % or less. In particular embodiments, the total amount of PEG incorporated into the polymer is from about 50 wt % to about 65 wt %, or from about 55 wt % to about 65 wt %. In particular embodiments, the total amount of PEG is about 56.3 wt %, about 57.0 wt %, about 59.0 wt %, 61.6 wt %, about 63.3 wt %, or about 64.0 wt %. Unless otherwise specified, a weight percentage of a particular component of the polymer means that the total weight of the polymer is made up of the specified percentage of monomers of that component. For example, 65 wt % PEG means that 65% of the weight of the polymer is made up of PEG monomers, which monomers are linked into blocks of varying lengths, which blocks are distributed along the length of polymer, including in a random distribution.

Since the PEG blocks contribute hydrophilicity to the polymer, increasing the length of the PEG blocks or the total amount of PEG in the polymer will tend to make the polymer more hydrophilic. Depending on the amounts and proportions of the other components of the polymer, the desired overall hydrophilicity, the desired CGC, and the nature and chemical functional groups of any drug or therapeutic agent that may be included in a formulation of the polymer, a skilled person can readily adjust the length (or $M_n$) of the PEG blocks used and/or the total amount of PEG incorporated into the polymer, in order to obtain a polymer having the desired physical and chemical characteristics.

The PPG blocks incorporated into the polymer may have a number average molecular weight ($M_n$) of about 10 000 g.mol$^{-1}$ or less, about 8 000 g.mol$^{-1}$ or less, about 5 000 g.mol$^{-1}$ or less, about 3 000 g.mol$^{-1}$ or less, about 2 000 g.mol$^{-1}$ or less, about 1 000 g.mol$^{-1}$ or less, about 800 g.mol$^{-1}$ or less, about 400 g.mol$^{-1}$ or less, or about 200 g.mol$^{-1}$ or less. In a particular embodiment, the PPG used has an $M_n$ of about 2 200 g.mol$^{-1}$ or less. PPGs of various sizes are commercially available and can readily be used in the present polymer.

The total amount of PPG in the polymer may be about 40 wt % or less, about 35 wt % or less, about 30 wt % or less, or about 25 wt % or less. In particular embodiments, the total amount of PPG incorporated into the polymer is from about 25 wt % to about 40 wt %, or from about 28 wt % to about 38 wt %. In particular embodiments, the total amount of PPG is about 28.3 wt %, about 27.0 wt %, about 29.7 wt %, about 33.9 wt %, about 35.7 wt %, or about 37.9 wt %.

By adjusting the length of the PPG segments and the total amount of PPG in the polymer, the hydrophilicity and hydrophobicity of the polymer at particular temperatures can be fine tuned, resulting in adjustment of the gelation temperature of the polymer. That is, higher amounts of PPG in the polymer tends to result in a polymer that gels at a lower temperature than a comparable polymer having lower amounts of PPG. Thus, depending on the application for which the polymer is intended and the conditions under which the polymer is desired to gel, a skilled person will be able to select the appropriate length and amount of PPG in the polymer to obtain a polymer with the desired properties. For example, if the polymer is to be injected in liquid form to form a gel within a subject's body, a gelation temperature of slight less than body temperature, for example human body temperature (37° C.), is likely preferable. However, if the polymer is to be used as scaffolding for tissue engineering, a gelation temperature around room temperature may be preferred.

Depending on the composition of a particular polymer, the present polymer will tend to have a gelation temperature in the range of from about 10° C. to about 70° C. In certain embodiments, the polymer has a gelation temperature equal to or less than about 37° C., or a gelation temperature less than about 37° C. In certain embodiments, the polymer has a gelation temperature equal to or less than about 22° C., or a gelation temperature less than about 22° C.

The molar ratio of total amount of PEG to total amount of PPG incorporated into the polymer may be about 2:1 PEG:PPG, or from about 1:1 to about 3:1. In various embodiments, the ratio of PEG:PPG is from about 1.4:1 to about 2.5:1, from about 1.7:1 to about 2.3:1, from about 1.9:1 to about 2.1:1. In particular embodiments, the ratio of PEG:PPG is about 1.5:1, about 1.6:1, about 1.9:1, about 2.0:1, about 2.1:1, or about 2.3:1. As used herein, molar ratio refers to the ratio of the molar content of the particular type of monomers included in the polymer. Thus, the molar ratio of PEG:PPG refers to the ratio of the molar amount of ethylene glycol monomers to the molar amount of propylene glycol monomers in a given polymer.

The PHB blocks incorporated into the polymer may have a number average molecular weight ($M_n$) of about 10 000 g.mol$^{-1}$ or less, about 8 000 g.mol$^{-1}$ or less, about 5 000 g.mol$^{-1}$ or less, about 3 000 g.mol$^{-1}$ or less, about 2 000 g.mol$^{-1}$ or less, about 1 100 g.mol$^{-1}$ or less, about 1 000 g.mol$^{-1}$ or less, about 500 g.mol$^{-1}$ or less, or about 200 g.mol$^{-1}$ or less. In a particular embodiment, the PPG used has an $M_n$ of about 2 800 g.mol$^{-1}$ or less or about 1 100 g.mol$^{-1}$ or less. PHBs of various sizes are commercially available and can readily be used in the present polymer.

The total amount of PIM in the polymer may be about 10 wt % or less, about 7 wt % or less, about 5 wt % or less, or about 2.5 wt % or less. In particular embodiments, the total amount of PHB incorporated into the polymer is from about 2 wt % to about 10 wt %. In particular embodiments, the total amount of PHB is about 2.1 wt %, about 5.1 wt %, about 7.1 wt %, or about 8.1 wt %.

By adjusting the length of the PHB segments and the total amount of PHB in the polymer, the amount of biodegradable material in the polymer can be adjusted, as well as the critical gelation concentration. PHB is hydrophobic, and the PHB blocks likely associated to form micelles in solution. It will be appreciated that if a PHB of higher $M_n$ is used, then the wt % of PHB used may be decreased, in order to obtain a soluble polymer. If the length of the PHB blocks, in combination with the total amount (wt %) of the PHB is too high, the polymer may not be soluble in aqueous solution.

Association of PHB blocks in solution allows for physical crosslinking of the PHB blocks to occur.

A particular order of the blocks within the polymer is not essential, and thus the present polymer may be a random polymer. Accordingly, the blocks of PEG, PPG and PHB need not be arranged in any particular order along the polymer backbone. As well, if there is a directionality to one or more of the blocks, any particular block may be incorporated in either orientation within the polymer backbone.

In certain embodiments, the molar ratio of total amount of PEG to total amount of PPG to total amount of PHB incorporated into the polymer may be in the range of about 0.1-10:1:0.01-1 PEG:PPG:PHB, or from about 0.1:1:1 to about 10:1:0.01 or from about 10:1:1 to about 0.1:1:0.01. In various embodiments, the ratio of PEG:PPG:PHB is from about 1:1:0.05 to about 5:1:0.05, from about 1:1:0.01 to about 1:1:1 or from about 1:1:0.5 to about 10:1:0.5. The molar ratio of PEG:PPG:PHB refers to the ratio of the molar amount of ethylene glycol monomers to the molar amount of propylene glycol monomers to the molar amount of 3-hydroxy butyric acid monomers in a given polymer.

The blocks may be linked together by any chemical linkage or functional group, including incorporation of any required chemical groups into the polymer backbone in order to link the blocks together. For example, in one particular embodiment, the PEG, PPG and PHB groups are linked by urethane linkages (also referred to as carbamate linkages). Creation of the urethane linkages may result in incorporation of a monomer containing the required reactive functional groups to form the linkages into the backbone. The monomer involved in linking the blocks is preferably biocompatible, but does not need to be biodegradable, given the presence of the PHB in the polymer. In one embodiment, alkylene groups, for example hexamethylene groups, may be incorporated, linked to adjacent PEG, PPG or PHB blocks by urethane linkages.

It will be apparent that linkages other than urethane linkages may be used to connect the blocks within the polymer. For example, any bi-functional species that contains two reactive groups that react with free hydroxyls may be used to link the blocks. In certain embodiments, the blocks in the polymer may be linked by one or more of ester, amide, urethane, carbonate, sulfone, anhydride, or sulphur-amide linkages.

The present polymer may be synthesized having various weight average and number average molecular weights, as desired. In various embodiments, the polymer has a molecular weight of about 1 000 to about 1 000 000 g.mol$^{-1}$. In various embodiments, the polymer has an $M_n$ of about 60 000 g.mol$^{-1}$ or less, about 55 000 g.mol$^{-1}$ or less, about 50 000 g.mol$^{-1}$ or less, about 45 000 g.mol$^{-1}$ or less, about 40 000 g.mol$^{-1}$ or less, about 35 000 g.mol$^{-1}$ or less, or about 30 000 g.mol$^{-1}$ or less. In particular embodiments, the present polymer has an $M_n$ of about 30 000 g.mol$^{-1}$ to about 52 000 g.mol$^{-1}$, or an $M_n$ of about 30 000 g.mol$^{-1}$, about 38 000 g.mol$^{-1}$, about 39 000 g.mol$^{-1}$, about 43 000 g.mol$^{-1}$, about 46 000 g.mol$^{-1}$, or about 51 000 g.mol$^{-1}$.

As mentioned above, the present polymers are biocompatible, meaning that the polymers are non-toxic and do not, or do not significantly irritate tissue or cause an inflammatory or immune response within the body. The PHB blocks are biodegradable, and can naturally be broken down to produce 3-hydroxybutyric acid, resulting in liberation of the blocks of PEG and PPG, which may then be easily cleared from the body.

The present polymer may possess a CGC at elevated temperatures that is much lower than values reported in the literature for other thermogelling polymers, for example Pluronic™ polymers. For example, aqueous solutions of various embodiments of the polymer undergo a sol-gel-sol transition as the temperature increases from about 4° C. to 80° C., and exhibit a low CGC ranging from about 2 to about 5 wt % in solution. In various embodiments, the polymer has a CGC from about 1% to about 10% (wt % in solution), about 2% to about 10% (wt % in solution), or about 2% to about 5% (wt % in solution). Particular embodiments have a CGC of about 2 wt %, about 3 wt %, about 4 wt %, about 5 wt % in solution or about 10 wt % in solution.

The combination of high molecular weight of the polymers and the incorporation of PHB segments into the amphiphilic polymers results in polymers with improved gel properties compared to the Pluronics™ polymers and/or other similar thermogelling systems.

As mentioned above, the presently described polymers may be synthesized using commercially available PEG, PPG and PHB to form the blocks within the multiblock polymer. Known chemistry techniques and known reactions may be used to link the blocks together to form the polymer. As mentioned above, the blocks may be connected by urethane linkages.

Thus, in one aspect, there is provided a method of manufacturing the present polymer, the method comprising reacting hydroxyl groups of PHB-diol, PEG and PPG with a diisocyanate. The diisocyanate acts a coupling agent, linking the PHB, PEG and PPG blocks via urethane linkages between the diisocyanate and a hydroxyl group on the end of a relevant block.

The PHB-diol may be synthesized as described (24-26). Briefly, PHB can be obtained commercially and can be transesterified to form PHB-diol (telechelic hydroxylated PHB), for example by using dibutyltin dilaurate as a catalyst in diglyme.

PHB-diol, PPG and PEG are mixed in the desired ratio under anhydrous conditions in a suitable solvent. For example, the solvent may be anhydrous dichloroethane.

A diisocyanate is added to the solution, at a molar ratio of isocyanate reactive groups to hydroxyl reactive groups of about 1:1. Any diisocyanate may be used, provided that the segment between isocyanate groups is not too short to sterically hinder the reaction of both isocyanate groups with a free hydroxyl group on a relevant block. Preferable the diisocyanate chosen is biocompatible, and may be biodegradable. In one particular embodiment, the diisocyanate is an alkylene diisocyanate, for example hexamethylene diisocyanate (HDI).

The reaction with the diisocyanate may be performed at elevated temperatures, for example between 50° C. and 80° C.

The resultant polymers may be isolated and purified from the reaction mixture using known techniques, for example by precipitation or by filtration.

The presently described polymer is useful for the delivery of drugs or other therapeutic agents to sites within a subject's body, or for use as scaffolding for tissue engineering applications, cell support matrices or as wound coverings. Thus, it may be desirable to incorporate various therapeutic agents, including drugs and growth factors, into compositions containing the polymer.

Thus, in one aspect there is provided a composition comprising the present polymer and a therapeutic agent.

The composition comprises sufficient concentration of the polymer to gel under desired conditions, which will depend in part on the CGC of the polymer. For example, the composition may comprise from about 1 wt % to about 20 wt % of the polymer, from about 2 wt % to about 10 wt % of the polymer, or from about 2 wt % to about 6 wt % of the polymer.

In certain embodiments, the composition is a solution at a temperature below the gelation temperature of the polymer, and forms a gel at or slightly above the gelation temperature of the polymer. Thus, the composition may further comprise a solvent. In certain embodiments the solvent is an aqueous solvent, and the composition is a hydrogel above the gelation temperature of the polymer.

The composition may further comprise a therapeutic agent. The therapeutic agent may be any compound that is to be delivered to cells in culture or is to be delivered within the body of a subject. For example, the therapeutic agent may be a nucleic acid, including DNA, a peptide, a protein, a small molecule, or a cell. The therapeutic agent may be an antibody, an antigen, a ligand, a hormone, a growth factor, a cell signalling molecule, a cytokine, an enzyme inhibitor. The therapeutic agent may be an antibiotic, a chemotherapeutic agent, an anti-inflammatory agent, an analgesic.

The concentration of therapeutic agent to be included in the composition will vary depending on the particular therapeutic agent, the site of delivery, the age, weight and sex of the subject and the particular reason for delivery of the therapeutic agent and may be routinely determined by one skilled in the art. Compositions can be prepared to contain an effective amount meaning the amount sufficient to achieve the desired effect.

The composition may further comprise a pharmaceutically acceptable diluent or carrier. In general, a diluent or carrier is selected on the basis of the mode and route of administration, and standard pharmaceutical practice. Suitable pharmaceutical carriers or diluents, as well as pharmaceutical necessities for their use in pharmaceutical formulations, are described in *Remington's Pharmaceutical Sciences*.

There is also provided a method of delivering a therapeutic agent to a subject, the method comprising delivering the present composition containing the polymer and a therapeutic agent to the body of a subject.

The composition may be delivered by implantation. For example, the composition may already be gelled prior to implantation and may be delivered by surgical implantation methods. Alternatively, the implantation may comprise injection of the composition in liquid form to a site within a subject's body, where the composition then gels upon equilibrating to the body temperature of the subject.

The subject may be any subject that is in need of receiving the therapeutic agent, including a mammal, including a human subject.

There is also contemplated use of the present polymer, including for the manufacture of a medicament, for delivering a therapeutic agent to the body of a subject.

The present polymers, methods, compositions and uses are further exemplified by the following non-limiting examples.

EXAMPLES

Example 1

Potentially biodegradable and biocompatible polymers comprising PHB, PEG and PPG connected by urethane linkages have been successfully synthesized. PEG and PPG molar ratios were fixed at approximately 2:1 various amounts of PHB were incorporated, using hexamethylene diisocyanate (HDI) as a coupling agent. The polymers chemical structure and molecular characteristics were studied with GPC, $^1$H NMR, $^{13}$C NMR and FTIR, which confirmed the architecture of the multiblock poly(PHB/PEG/PPG urethane)s. The GPC results indicated that the synthesized poly(PHB/PEG/PPG urethane)s had high molecular weights with relatively narrow molecular weight distributions. The contents of PHB segment in the poly(PHB/PEG/PPG urethane)s calculated from $^1$H NMR ranged from 2.1 to 12.7 wt %.

The thermal stability of the poly(PHB/PEG/PPG urethane)s was studied by TGA, and three separate thermal degradation steps corresponding to PHB, PPG, and PEG segments were observed, from which the PHB contents were calculated and the results were in good agreement with those from the $^1$H NMR measurements. The poly(PHB/PEG/PPG urethane)s presented better thermal stability than the PHB precursors.

The CMC values of the water-soluble copolymers were determined by the dye solubilization method. The CMC values of the copolymers in this work ranged from $5.16 \times 10^{-4}$ to $9.79 \times 10^{-4}$ g.mol$^{-1}$. On the basis of the dye solubilization and $^{13}$C NMR experiments, the micelle is concluded to have a hydrophobic core made up of PHB and PPG segments and an outer hydrophilic corona of PEG.

The sol-gel transitions of the aqueous copolymers were studied and a phase diagram showing the various soluble and gel regions as a function of temperature and concentration of the solution were generated. The critical gelation concentration of the copolymers in this work ranged from 2-5 wt %. $^{13}$C NMR of the gel solution was obtained at various temperatures. From the profiles of the NMR spectra, the sol-gel transition can be elucidated, offering method of studying the sol-gel transition at a molecular level. The viscosities of the EPH2 gel at various concentrations were studied and were found to be higher than the Pluronics F127 gel (20 wt %), even at the critical gelation concentration of 2 wt %.

Materials.

Natural source poly[(R)-3-hydroxybutyrate] (PHB) was supplied by Aldrich, and purified by dissolving in chloroform followed by filtration and subsequent precipitation in hexane before use. The $M_n$ and $M_w$ of the purified PHB were $8.7 \times 10^4$ and $2.3 \times 10^5$, respectively. Poly(ethylene glycol) (PEG) and poly(propylene glycol) (PPG) with $M_n$ of ca. 2000 was purchased from Aldrich. Purification of the PEG was performed by dissolving in dichloromethane followed by precipitation in diethyl ether and vacuum dried before use. Purification of PPG was performed by washing in hexane three times and vacuum dried before use. The $M_n$ and $M_w$ of PEG were found to be 1890 and 2060, respectively. The $M_n$ and $M_w$ of PPG were found to be 2180 and 2290, respectively. Bis(2-methoxyethyl)ether (diglyme, 99%), ethylene glycol (99%), dibutyltin dilaurate (95%) 1,6-hexamethylene diisocyanate (HDI) (98%), methanol, diethyl ether, 1,2-dichloroethane (99.8%) and 1,6-diphenyl-1,3,5-hexatriene (DPH) were purchased from Aldrich. Diglyme was dried with molecular sieves, and 1,2-dichloroethane was distilled over CaH$_2$ before use.

Synthesis of Poly(PHB/PEG/PPG Urethane)s.

Telechelic hydroxylated PHB (PHB-diol) prepolymers with various molecular weight were prepared by transesterification between the natural source PHB and ethylene glycol using dibutyltin dilaurate in diglyme as reported previously (24-26). The yields were about 80%. Poly(PHB/PEG/PPG urethane)s were synthesized from PHB-diol, PEG and PPG with molar ratios of PEG/PPG fixed at approximately 2:1 and PHB content ranging from 5 to 20 mol % (calculated from the $M_n$ of PHB-diol) using HDI as a coupling reagent. The amount of HDI added was equivalent to the reactive hydroxyl groups in the solution. Typically, 0.064 g of PHB-diol ($M_n$=1070, $6.0 \times 10^{-5}$ mol), 1.44 g of PEG ($M_n$=1890, $7.6 \times 10^{-4}$ mol) and 0.82 g of PPG ($M_n$=2180, $3.8 \times 10^{-4}$ mol) were dried in a 250-ml two-neck flask at 50° C. under high vacuum overnight. Then, 20 ml of anhydrous 1,2-dichloroethane was added to the flask and any trace water in the system was removed through azeotropic distillation with only 1 ml of 1,2-dichloroethane being left in the flask. When the flask was cooled down to 75° C., 0.20 g of HDI ($1.2 \times 10^{-3}$ mol) and two drops of dibutyltin dilaurate ($\sim 8 \times 10^{-3}$ g) were added sequentially. The reaction mixture was stirred at 75° C. under a nitrogen atmosphere for 48 hrs. The resultant copolymer was precipitated from diethyl ether, and further purified by redissolving into 1,2-dichloroethane followed by precipitation in a mixture of methanol and diethyl ether to remove remaining dibutyltin dilaurate. A series of poly(PHB/PEG/PPG urethane)s with different compositions of PHB were prepared, and their number-average molecular weight and polydispersity values are given in Table 1. The yield was 80% and above after isolation and purification. $^1$H NMR (CDCl$_3$) of poly (PHB/PEG/PPG urethane)s EPH2: δ (ppm) 1.14 (—O(C H$_3$)CHCH$_2$O—), 1.26 (—O(CH$_3$)CHCH$_2$CO—), 1.32 (—OOCNHCH$_2$CH$_2$CH$_2$CH$_2$CH$_2$NHCOO—), 1.48 (—OOCNHCH$_2$CH$_2$CH$_2$CH$_2$CH$_2$CH$_2$NHCOO—), 2.44-2.63 (—O(CH$_3$)CHCH$_2$CO—), 3.13 (—OOCNHC H$_2$CH$_2$CH$_2$CH$_2$CH$_2$NHCOO—), 3.41 (—O(CH$_3$)C HCH$_2$O—), 3.46 (—O(CH$_3$)CHCHH$_2$O—), 3.64 (—OC H$_2$CH$_2$O—), 4.20 (—OOCNHCH$_2$CH$_2$CH$_2$CH$_2$CH$_2$N HCOO—), 5.21-5.29 (—O(CH$_3$)CHCH$_2$CO—). $^{13}$C NMR of EPH2 (CDCl$_3$) of poly(PHB/PEG/PPG urethane)s: δ (ppm) 17.77 (—O(CH$_3$)CHCH$_2$O—), 20.14 (—O( CH$_3$)CHCH$_2$CO—), 26.69 (—OOCNHCH$_2$CH$_2$CH$_2$ CH$_2$CH$_2$NHCOO—), 30.26 (—OOCNHCH$_2$ CH$_2$CH$_2$CH$_2$CH$_2$NHCOO—), 41.20 (—O(CH$_3$)CH CH$_2$CO—), 64.18 (—OOCNHCH$_2$CH$_2$CH$_2$CH$_2$ CH$_2$NHCOO—), 67.99 (—O(CH$_3$)CHCH$_2$CO—), 70.94 (—OCH$_2$CH$_2$O—), 73.56 (—O(CH$_3$)CHCH$_2$O—), 75.72 (—O(CH$_3$)CHCH$_2$O—), 156.82 (—OO CNHCH$_2$CH$_2$CH$_2$CH$_2$CH$_2$CH$_2$NHCOO—), 169.98 (—OO (CH$_3$)CHCH$_2$CO—).

TABLE 1

| | Molecular Characteristics of Poly(PHB/PEG/PPG urethane)s | | | | | | | | | |
|---|---|---|---|---|---|---|---|---|---|---|
| | $M_n$ of PHB used[b] | Feed ratio (wt %) | | | Composition in copolymer (wt %)[c] | | | Copolymer characteristics | | cmc[d] |
| Copolymer[a] | (g mol$^{-1}$) | PHB | PEG | PPG | PHB | PEG | PPG | $M_n^b$ (×10$^3$) | $M_w/M_n^b$ | (g/mL) |
| EPH1 | 1070 | 2.8 | 61.7 | 35.5 | 2.1 | 64.0 | 33.9 | 50.6 | 1.56 | $9.79 \times 10^{-4}$ |
| EPH2 | 1070 | 5.6 | 59.9 | 34.5 | 5.1 | 57.0 | 37.9 | 45.5 | 1.38 | $8.69 \times 10^{-4}$ |
| EPH3 | 1070 | 8.7 | 58.0 | 33.4 | 8.1 | 56.3 | 35.7 | 42.5 | 1.37 | $5.16 \times 10^{-4}$ |
| EPH4 | 1070 | 11.8 | 55.9 | 32.2 | 11.4 | 61.6 | 27.0 | 37.8 | 1.16 | —[e] |

TABLE 1-continued

Molecular Characteristics of Poly(PHB/PEG/PPG urethane)s

| Copolymer[a] | $M_n$ of PHB used[b] (g mol$^{-1}$) | Feed ratio (wt %) | | | Composition in copolymer (wt %)[c] | | | Copolymer characteristics | | cmc[d] (g/mL) |
|---|---|---|---|---|---|---|---|---|---|---|
| | | PHB | PEG | PPG | PHB | PEG | PPG | $M_n{}^b$ (×10$^3$) | $M_w/M_n{}^b$ | |
| EPH5 | 2800 | 6.9 | 59.1 | 34.0 | 7.1 | 63.3 | 29.7 | 39.2 | 1.18 | 8.88 × 10$^{-4}$ |
| EPH6 | 2800 | 13.6 | 54.8 | 31.6 | 12.7 | 59.0 | 28.3 | 30.0 | 1.20 | —[e] |

[a]Poly(PHB/PEG/PPG urethane)s are denoted EPH, E for PEG, P for PPG and H for PUB.
The $M_n$ of PEG and PPG used for the copolymer synthesis was 1890 and 2180 g mol$^{-1}$, respectively.
[b]Determined by GPC.
[c]Calculated from $^1$H NMR results.
[d]Critical micellization concentration (cmc) in water determined by the dye solubilization technique at 25° C.
[e]Copolymers not water-soluble.

Molecular Characterization.

Gel permeation chromatography (GPC) analysis was carried out with a Shimadzu SCL-10A and LC-8A system equipped with two Phenogel 5μ 50 and 1000 Å columns (size: 300×4.6 mm) in series and a Shimadzu RID-10A refractive index detector. THF was used as eluent at a flow rate of 0.30 ml/min at 40° C. Monodispersed poly(ethylene glycol) standards were used to obtain a calibration curve. The $^1$H NMR (400 MHz) and $^{13}$C NMR (100 MHz) spectra were recorded on a Bruker AV-400 NMR spectrometer at room temperature. The $^1$H NMR measurements were carried out with an acquisition time of 3.2 s, a pulse repetition time of 2.0 s, a 30° pulse width, 5208 Hz spectral width, and 32K data points. Chemical shift was referred to the solvent peaks (δ=7.3 ppm for CHCl$_3$). Fourier transform infrared (FTIR) spectra of the polymer films coated on CaF$_2$ plate were recorded on a Bio-Rad 165 FT-IR spectrophotometer; 64 scans were signal-averaged with a resolution of 2 cm$^{-1}$ at room temperature.

Thermal Analysis.

Thermogravimetric analyses (TGA) were carried out on a TA Instruments SDT 2960. Samples were heated at 20° C. min$^{-1}$ from room temperature to 800° C. in a dynamic nitrogen atmosphere (flow rate=70 ml min$^{-1}$).

Critical Micellization Concentration (CMC) Determination.

The CMC values were determined by using the dye solubilization method (27, 28). The hydrophobic dye 1,6-diphenyl-1,3,5-hexatriene (DPH) was dissolved in methanol with a concentration of 0.6 mM. 20 μL of this solution was mixed with 2.0 mL of copolymer aqueous solution with concentrations ranging from 0.0001 to 0.5 wt % and equilibrated overnight at 4° C. A UV-Vis spectrophotometer was used to obtain the UV-Vis spectra in the range of 330-430 nm at 25° C. The CMC value was determined by the plot of the difference in absorbance at 378 nm and at 400 nm ($A_{378}$-$A_{400}$) versus logarithmic concentration.

Sol-Gel Transition.

The sol-gel transition was determined by a test tube inverting method with temperature increments of 2° C. per step (22a, 29). Each sample of a given concentration was prepared by dissolving the polymer in distilled water in a 2-mL vial. After equilibration at 4° C. for 24 h, the vials containing samples were immersed in a water bath at a constant designated temperature for 15 min. The gelation temperature was characterized by the formation of a firm gel that remained intact when the tube was inverted by 180° (30). Viscosities of the hydrogels were measured at 25° C. using a Brookfield HADV-III+ digital viscometer coupled to a temperature-controlling unit. The small sample adapters SSA 15/7R was used. The revolution rate of the spindle was set at 20 cycles min$^{-1}$ and shear rate was set at 9.6 s$^{-1}$.

Rheology Studies.

Viscosities of the hydrogels were measured at 25° C. using a Brookfield HADV-III+ digital viscometer coupled to a temperature-controlling unit. The small sample adapters SSA 15/7R was used. The revolution rate of the spindle was set at 20 cycles.min$^{-1}$ and shear rate was set at 9.6 s$^{-1}$.

Figure 11:
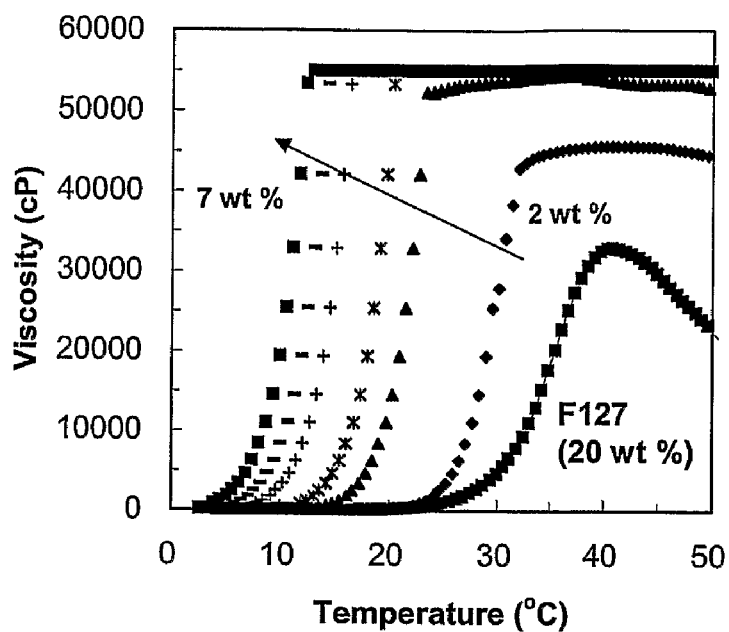
FIG. 11 is viscosity versus temperature curves of different concentrations of EPH2 in aqueous solution (2-7 wt %) in comparison with Pluronics F127 (20 wt %) at shear rate of 9.6 s$^{-1}$.

Drug release experiments. Aqueous solutions comprising of 5% (w/v) copolymer were mixed and left to equilibrate overnight at 4° C. Appropriate amounts of BSA were loaded to make the concentration of BSA in the polymer solution 5 mg.mL$^{-1}$. For comparison, 30% (w/v) of Pluronics F127 in aqueous solutions was prepared. The concentration of BSA in these solutions was also 5 mg.mL$^{-1}$. 1 mL of polymer solutions were injected into porous cellulose membranes (pore size: about 100 μm) and left to equilibrate at 37° C. The polymer slabs obtained had dimensions of (10 mm×25 mm×4 mm) and were placed in 25 mL of phosphate buffer release solutions. Fresh batches of release solutions were replaced at various time intervals. Experiments were done in triplicate. The resultant solutions were lyophilized and lyophilized samples were kept at −80° C. FIG. 11 illustrates BSA protein release profiles from the poly(PHB/PEG/PPG urethane) copolymer hydnogels in comparison with the Pluronic F127 hydrogel (Legend: A: EPH1, U: EPH2, x: EPH3 +: Pluronics F127).

Results and Discussion

Synthesis and Characterization of Poly(PHB/PEG/PPG Urethane)s.

Previously, we reported the synthesis and biodegradation behaviour of amphiphilic multiblock poly(ether ester urethane)s consisting of PEG and PUB blocks (24-26). These water-insoluble copolymers could not undergo a sol-gel transition and were non-thermosensitive. However, in this study, water-soluble and therraosensitive poly(PHB/PEG/PPG urethane)s were synthesized, and for the first time PHB has been incorporated into a thermogelling copolymer, to enhance the gel properties as well as to make the copolymers biodegradable.

Telechelic hydroxylated PUB (PHB-diol) with lower molecular weight were obtained through transesterification between high-molecular-weight natural source PHB and ethylene glycol using dibutyltin dilaurate as catalyst (24). The transesterification reaction was allowed to proceed for a few hours to overnight to produce PHB-diols with $M_n$ of 1070, and 2800, respectively, as determined by GPC. The reaction of hydroxyl groups of PHB-diol, PEG and PPG with isocyanate of 1,6-hexamethlyene diisocyanate (HDI) in the presence of dibutyltin dilaurate led to formation of poly(PHB/PEG/PPG urethane)s. The procedures for the synthesis of PHB-diol and poly(PHB/PEG/PPG urethane)s are presented in FIG. 1. Owing to the moisture sensitive nature, any trace water in the system was removed through azeotropic distillation, and the reaction was carried out in dried 1,2-dichloroethane under a nitrogen atmosphere. The target poly(PHB/PEG/PPG urethane)s were isolated and purified from the reaction mixture by repeated precipitation from a mixture of methanol and diethyl ether.

Figure 2:
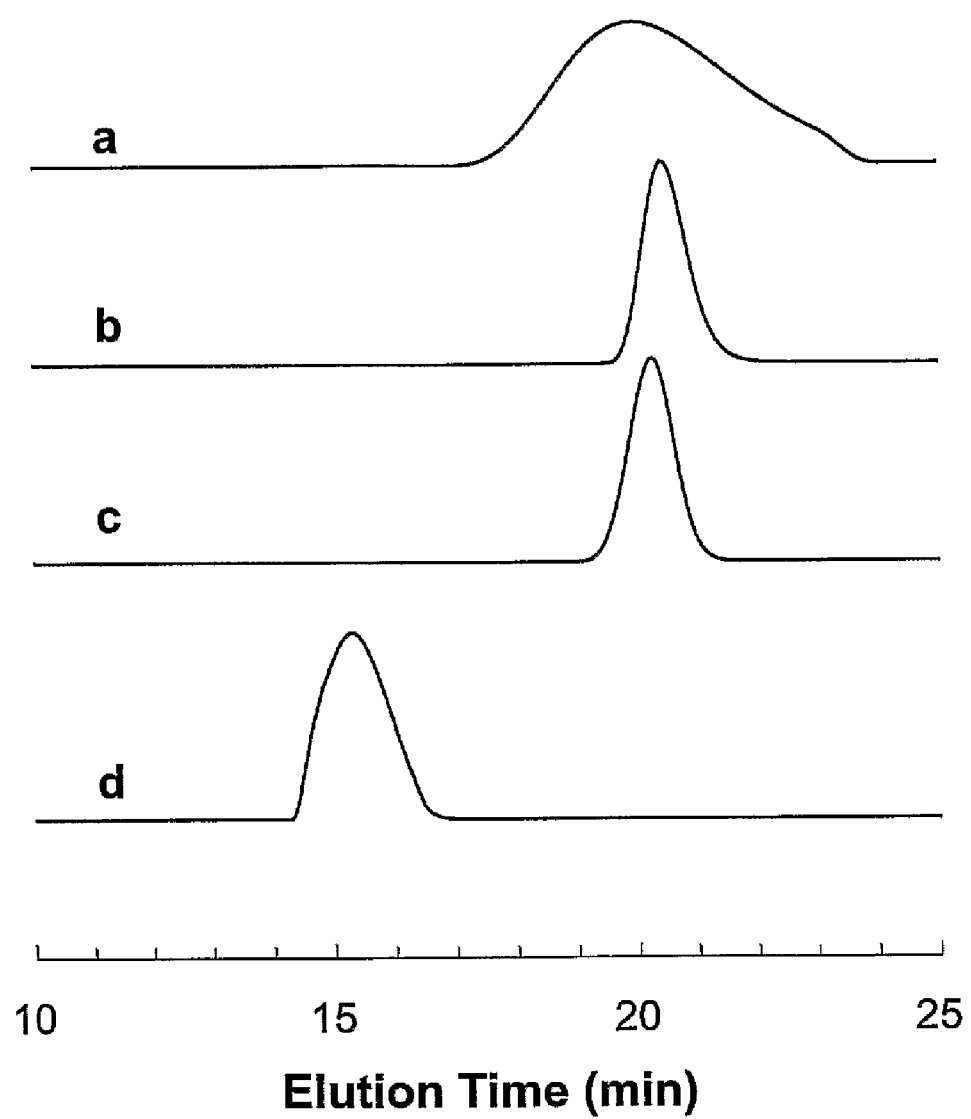
FIG. 2 are GPC diagrams of EPH2 and its PHB, PEG, and PPG precursors: (a) PHB-diol ($M_n$ 1080); (b) PEG ($M_n$ 1890); (c) PPG ($M_n$ 2180); and (d) EPH2 (M, $62.8 \times 10^3$, $M_n$ $45.5 \times 10^3$, $M_w/M_n$ 1.38)

A series of random multiblock poly(PHB/PEG/PPG urethane)s with different amounts of PHB incorporated were synthesized, and their molecular weights and molecular weight distributions were determined by GPC (Table 1). A typical GPC chromatograph for one of the poly(PHB/PEG/PPG urethane)s together with its corresponding precursors is shown in FIG. 2. The observation of unimodal peak in GPC chromatograph of the purified poly(PHB/PEG/PPG urethane) with non-overlapping nature with those of corresponding precursors indicates that a complete reaction took place with no unreacted precursor remaining (24-26). All the poly(PHB/PEG/PPG urethane)s synthesized had narrow molecular weight distribution and high molecular weight, with polydispersity ranging from 1.16 to 1.56 and $M_n$ $3.00 \times 10^4$ to $5.06 \times 10^4$. The results are tabulated in Table 1.

Figure 3A:
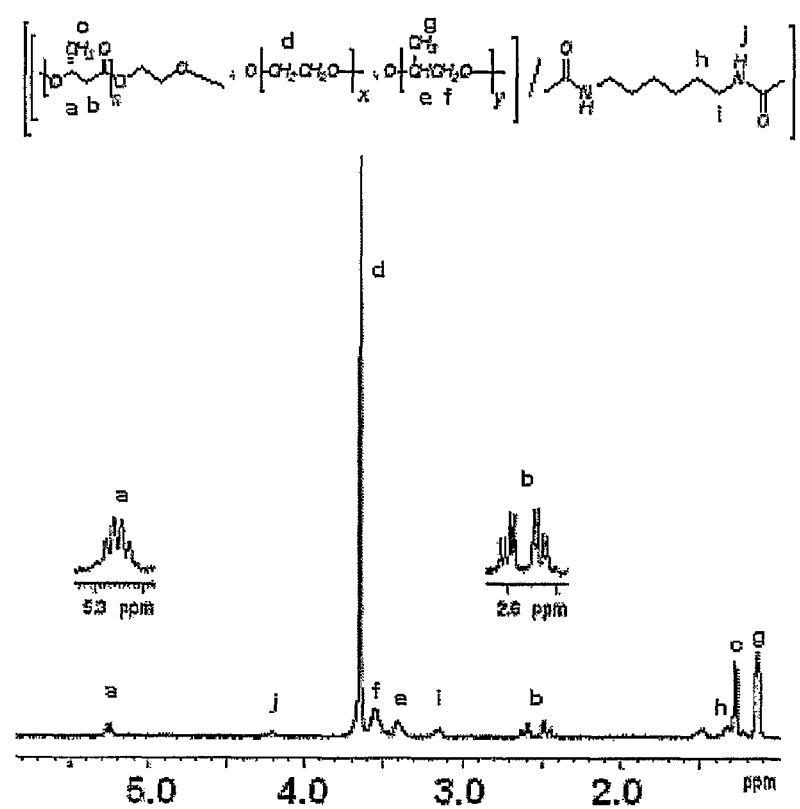
FIG. 3 (A) 400 MHz $^1$H NMR and (B) 100 MHz $^{13}$C NMR spectra of EPH2 in CDCl$_3$.

The chemical structure of poly(PHB/PEG/PPG urethane)s was verified by $^1$H NMR and $^{13}$C NMR spectroscopy (FIG. 3a & b). FIG. 3a shows the $^1$H NMR spectrum of EPH2 in CDCl$_3$, in which all proton signals belonging to each of PHB, PEG and PPG segments are confirmed. Signals corresponding to methylene protons in repeated units of PEG segments are observed at 3.64 ppm, the signals at 5.25 ppm are assigned to methine protons in the repeated unit of PHB segments (24-26), the signals at 1.14 ppm are assigned to the methyl protons of PPG. As the content of HDI among the starting materials is below 1 wt %, the compositions of the poly(PHB/PEG/PPG urethane)s could be determined from the integration ratio of resonances at 1.14, 3.64 and 5.25 ppm within the limits of $^1$H NMR precision, and the results are shown in Table 1.

Figure 3B:
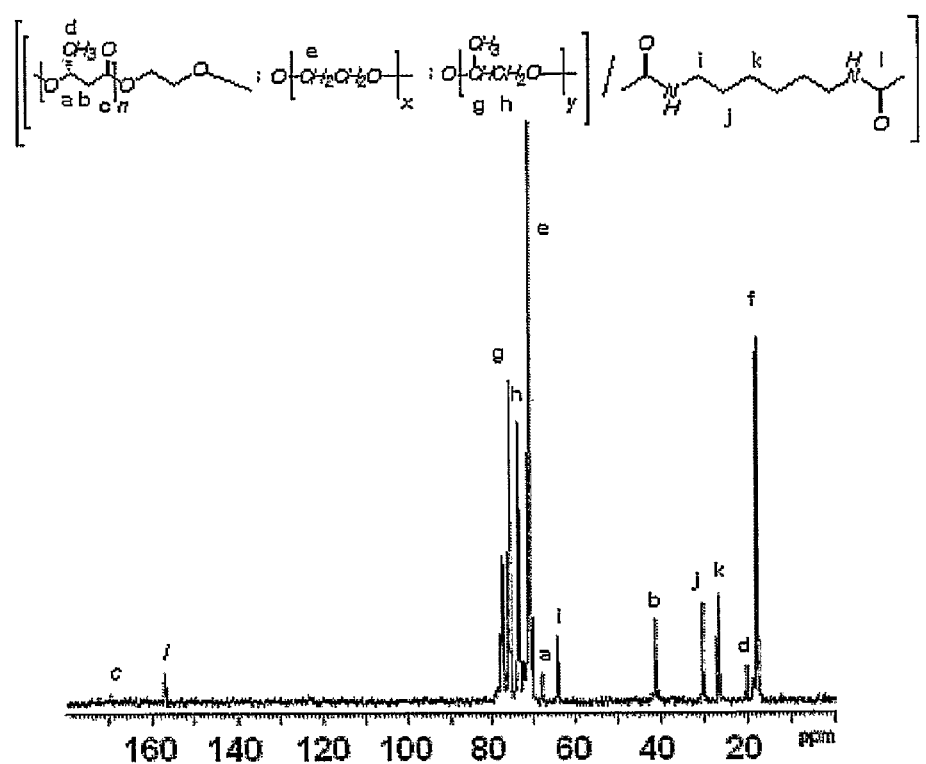

The $^{13}$C NMR was used to ascertain the chemical composition of the poly(PHB/PEG/PPG urethane)s. The peak assignments of the copolymers were performed by comparison with the $^{13}$C NMR spectra of the precursors. FIG. 3b shows the $^{13}$C NMR spectra of EPH2 in CDCl$_3$. Briefly, peaks at 17.77 (methyl C), 73.56 (methylene C) and 75.72 ppm (methine C) are assigned to the PPG moiety. A peak at 70.94 ppm is assigned to the methylene C of the PEG segment. Peaks at 20.14 (methyl C), 41.20 (methylene C), 67.99 (methine C) and 169.98 ppm (carbonyl C) are attributed to the PHB segment. In addition, peaks due to the HDI junction unit could be observed in the spectra (26.69, 30.26, 64.18 and 156.82 ppm).

A $^{13}$C NMR spectrum of hexamethylene diisocyanate was obtained and the carbonyl carbon peak was observed at 122.85 ppm. After the polymerization reaction, the $^{13}$C peak of the carbonyl carbon of the newly formed urethane linkage was observed at 156.82 ppm. This shift was attributed to the attachment of the hydroxyl groups to the isocyanate functional groups in the formation of the urethane linkage (—NCO—→—NHCOO—). This observation, together with the concomitant increase in the molecular weight of the copolymers indicates that the polycondensation reaction was successful.

Figure 4:
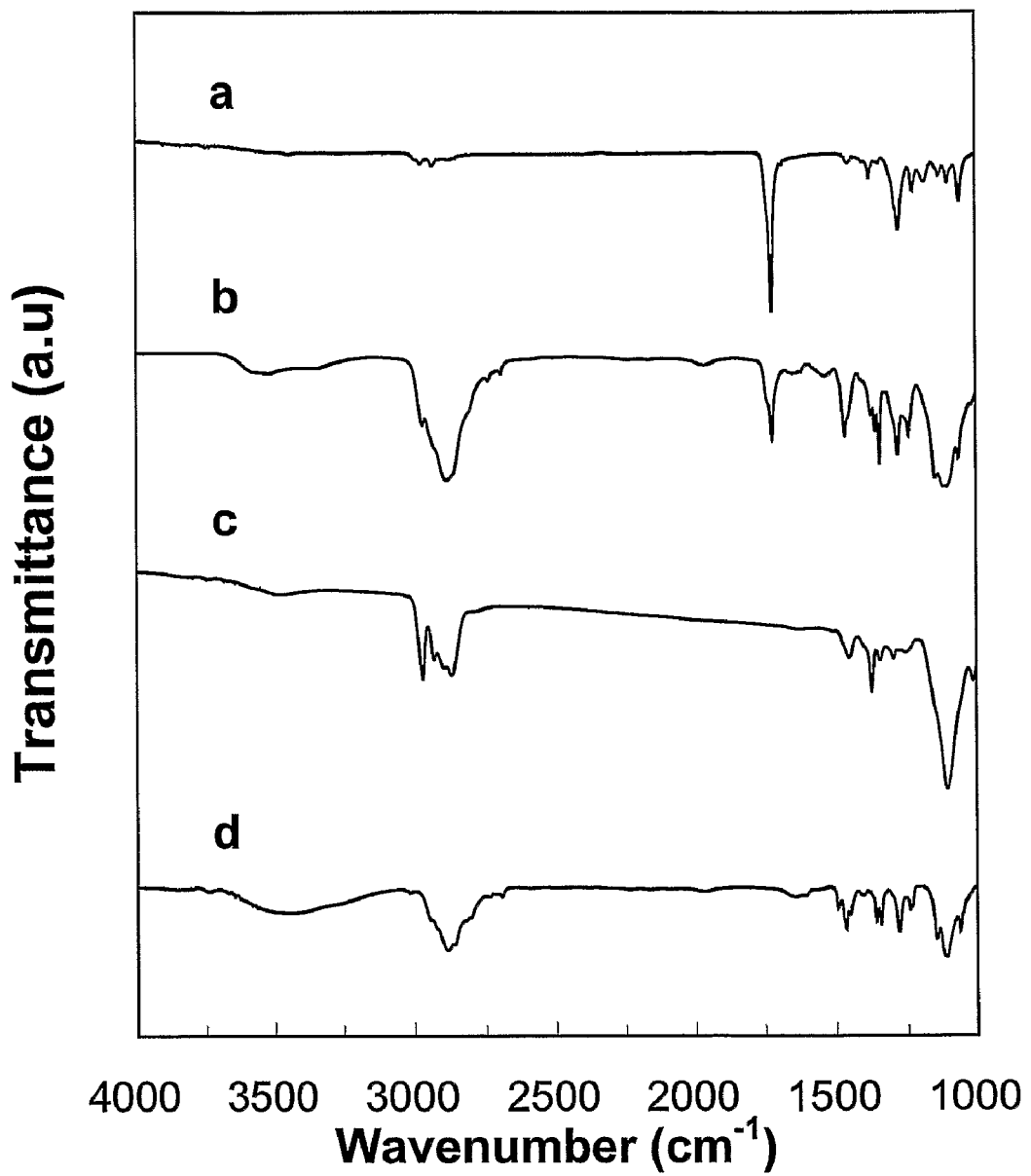
FIG. 4 is FTIR spectra of EPH2 and its PHB, PEG and PPG precursors: (a) PHB-diol ($M_n$ 1080); (b) EPH2; (c) PPG ($M_n$ 2180); and (d) PEG ($M_n$ 1890)

FTIR is useful in the characterization of the functional groups present in the polymer. As a typical example, FIG. 4 shows FTIR spectra of EPH2 and its PEG, PPG and PHB, precursors. For PPG (FIG. 4c) and PEG (FIG. 4d), the characteristic C—O—C stretching vibration of the repeated —OCH$_2$CH$_2$— units is observed at 1102 cm$^{-1}$. An intensive carbonyl stretching band at 1723 cm$^{-1}$ characterizes the FTIR spectrum of pure PHB-diol as shown in FIG. 4a. It is clearly seen that in FIG. 4b, all the characteristic absorptions for PHB-diol, PEG and PPG appear in the spectrum of EPH2, which confirms the presence of the three segments in the poly(PHB/PEG/PPG urethane)s. Furthermore, it can be seen in the profile of EPH2 that the peak ascribed to the —NCO— stretching was not observed in the region around 2200 cm$^{-1}$. This provides evidence that the isocyanate groups of the junction units have been reacted and are not present in the polymer product. These observations, together with the aforementioned evidences (GPC and NMR results) provide a solid justification for the successful synthesis of the multiblock copolymers.

Thermal Properties.

Figure 5:
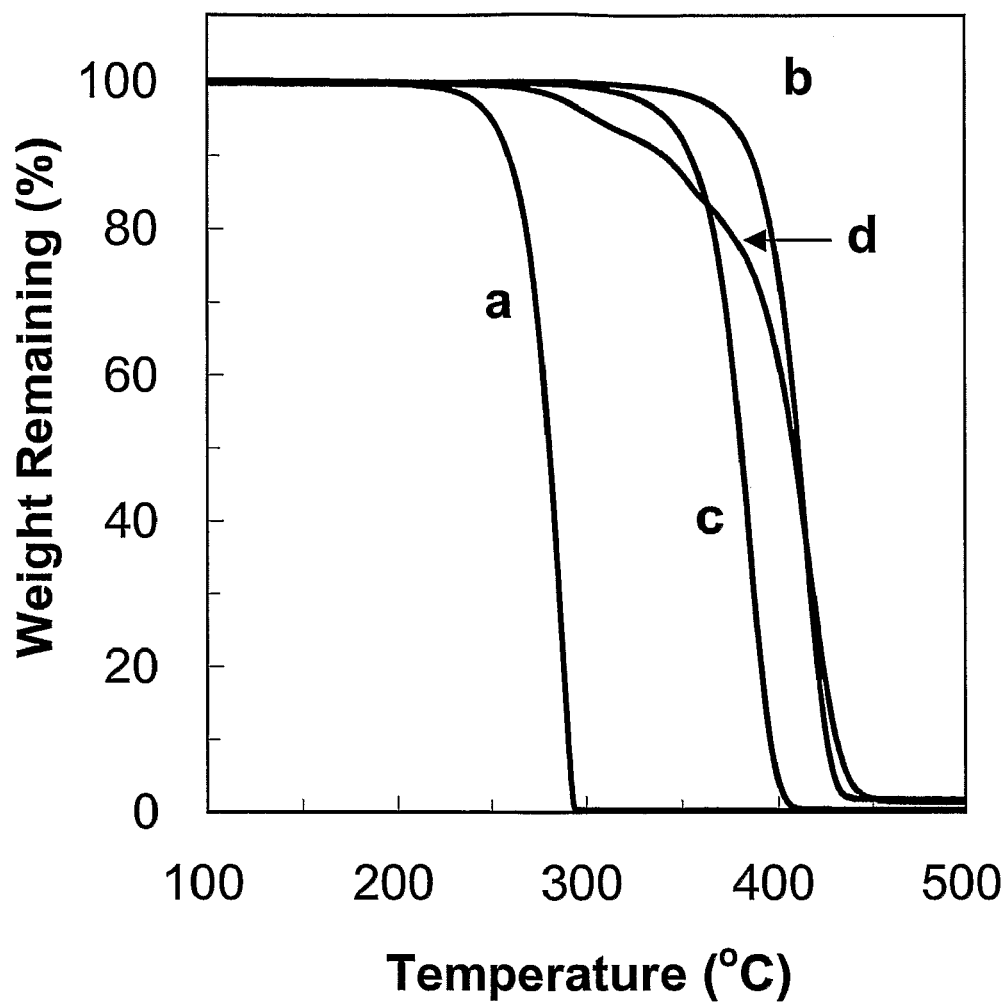
FIG. 5 is TGA curves of EPH2 and its PHB, PEG and PPG precursors: (a) PHB-diol ($M_n$ 1080); (b) PEG ($M_n$ 1890); (c) PPG ($M_n$ 2180); and (d) EPH2.

The thermal stability of poly(PHB/PEG/PPG urethane)s was evaluated using thermogravimetric analysis (TGA). FIG. 5 shows the TGA scan results for EPH2 compared with its PHB, PEG and PPG precursors. The degradation of pure PHB-diol starts at 218° C. and completes at 295° C. (FIG. 5a), PPG starts to degrade at 350° C. (FIG. 5c) while that of pure PEG starts at 400° C. (FIG. 5b), at which pure PHB-diol has completed the degradation. EPH2 undergoes a three-step thermal degradation with the first step occurring between 227 and 303° C. and the second and third steps between 350 and 433° C. (FIG. 5d). In comparison with the TGA curves of pure PHB-diol and pure PEG, the first weight loss step is attributed to the decomposition of PHB segment and the second and third weight loss step to the decomposition of both the PEG and PPG segments. However, the second and third weight loss steps are too close for the accurate determination of the compositions of PPG and PEG separately. Therefore, only the PHB content of EPH2 could be determined from the degradation profile. Similar weight loss curves were also observed for other poly(PHB/PEG/PPG urethane)s. The PHB contents estimated from TGA results are in good agreement with those calculated from $^1$H NMR.

Critical Micellization Concentration (CMC) Determination.

Figure 6:
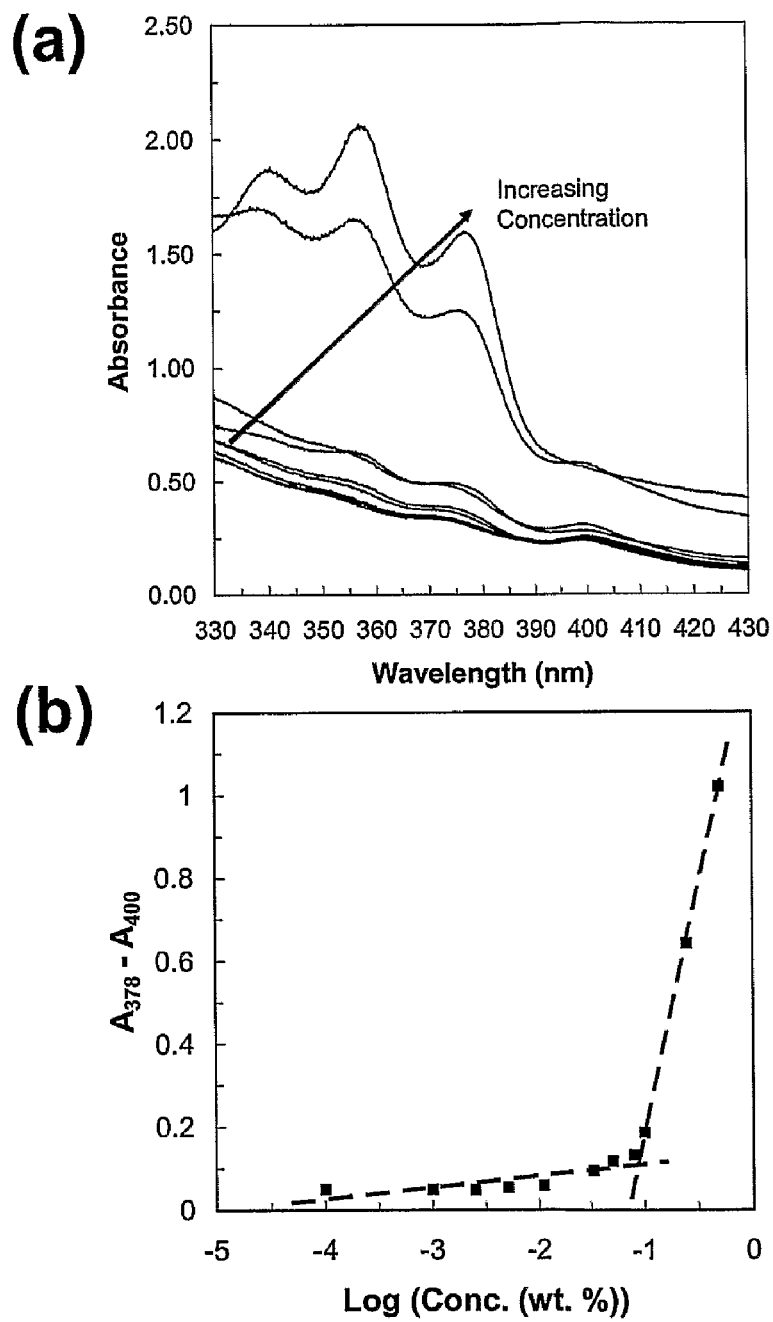
FIG. 6 is a) UV-vis spectra changes of DPH with increasing EPH2 copolymer concentration in water at 25° C. DPH concentration was fixed at 6 mM and the polymer concentration varied between 0.0001 and 0.5 wt %. The increase in the absorbance band at 378 nm indicates the formation of a hydrophobic environment in water; and b) CMC determination by extrapolation of the difference in absorbance at 378 nm and 400 nm.

Of the 6 poly(PHB/PEG/PPG urethane)s, only EPH1, EPH2, EPH3 and EPH5 were soluble in water. The CMC determination was carried out for these four copolymers. This experiment was conducted by varying the aqueous polymer concentration in the range of 0.0001 to 0.5 wt %, while keeping the concentration of DPH constant. DPH shows a higher absorption coefficient in a hydrophobic environment than in water. Thus, with increasing polymer concentration, the absorbances at 344, 358 and 378 nm increased (FIG. 6a). The point where the absorbance suddenly increases corresponds to the concentration at which micelles are formed. When the micelle is formed, DPH partitions preferentially into the hydrophobic core formed in the aqueous solution (22a, 27-29). The CMC was determined by extrapolating the absorbance at 378 nm minus the absorbance at 400 nm ($A_{378}$-$A_{400}$) versus logarithmic concentration (FIG. 6b). The CMC values for the water-soluble copolymers are tabulated in Table 1 and are in the range of $5.16 \times 10^{-4}$ to $9.79 \times 10^{-4}$ g. mL$^{-1}$. Comparing the copolymers of similar molecular weights, the CMC values are much lower than that reported by Ahn et al. for a series of multiblock poloxamer copolymers (19), showing that the incorporation of PHB greatly increases the hydrophobicity of the copolymers, resulting in a decrease in the CMC values.

Figure 7:
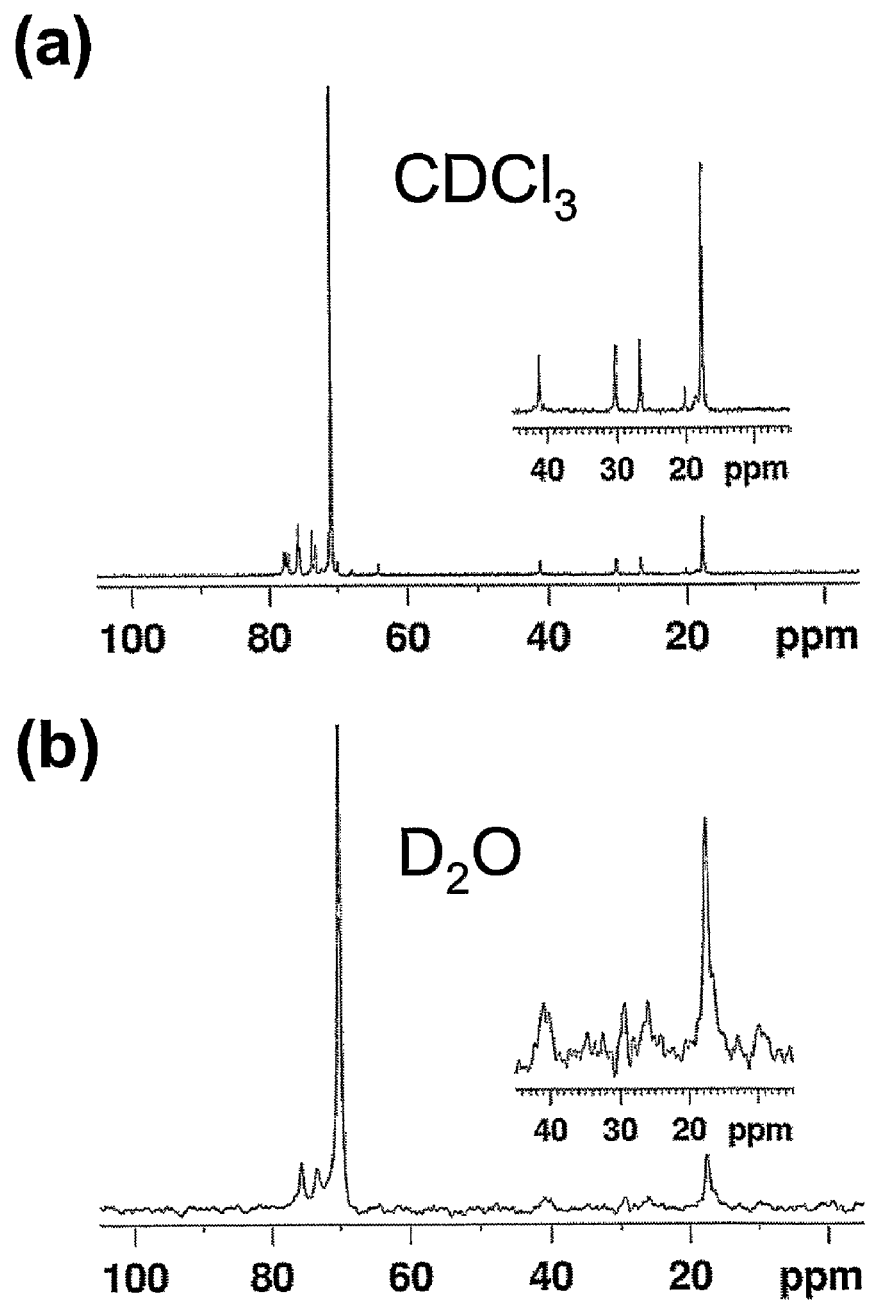
FIG. 7 is $^{13}$C NMR spectra of EPH2 (5 wt %) in (a) CDCl$_3$ and (b) D$_2$O at 25° C.
Figure 8:
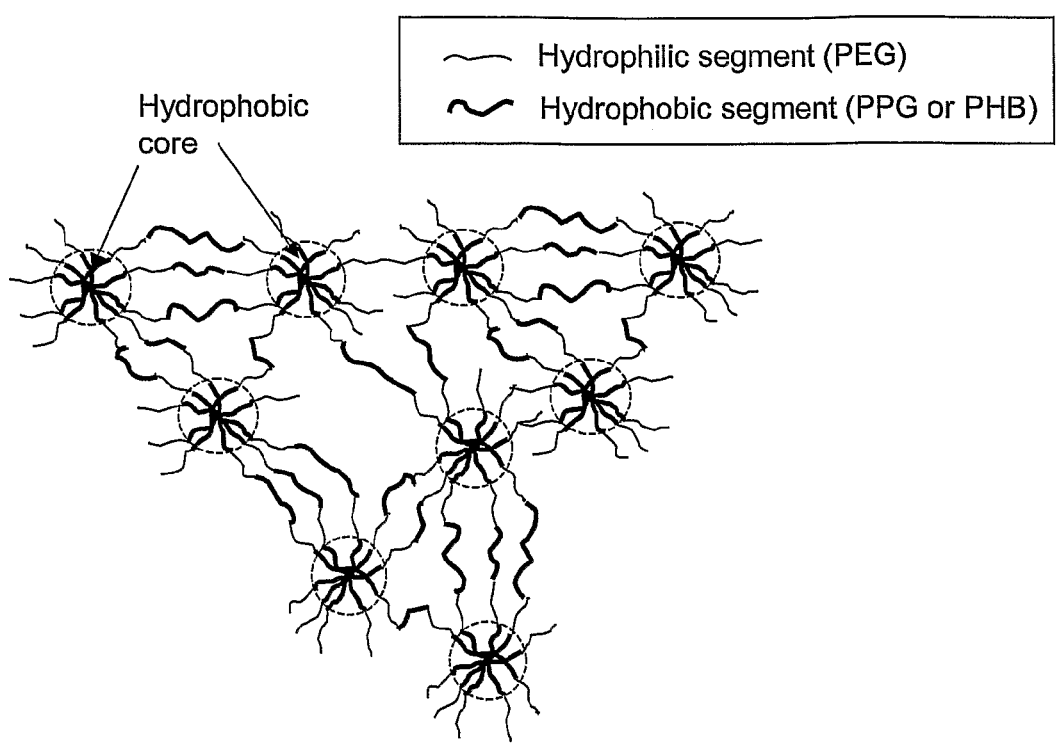
FIG. 8 is a schematic depiction of an associated micelle model showing the network-like packing of the polymer chains.

The $^{13}$C NMR was used to investigate the effect of solvent on the micelle structure (29, 31-34). CDCl$_3$ is a good nonselective solvent for PHB, PEG and PPG while water is a good selective solvent for PEG but poor for PPG and PHB. As shown in FIG. 7, in CDCl$_3$, the peaks due to the PHB, PEG and PPG were sharp and well defined. In D$_2$O, PEG is shown as a sharp peak but the PHB and the PPG peaks are collapsed and broadened. This shows that the molecular motion of PHB and PPG is slow in water, indicating a hydrophobic core structure made up of PHB and PPG with PEG as the outer corona structure, confirming the core-corona structure of the micelle (31-33). However, in the light of the multiblock architecture of the copolymers, it is not reasonable to expect that the simple micelles of an ABA-type amphiphilic polymer be formed. Instead, it would be more plausible to consider an associated micelle model in the consideration of the above results. An associated micelle structure could be formed by the network-like packing of the polymer chains, as illustrated in FIG. 8.

Thermo-Reversible Sol-Gel Transition of the Copolymers.

Figure 9:
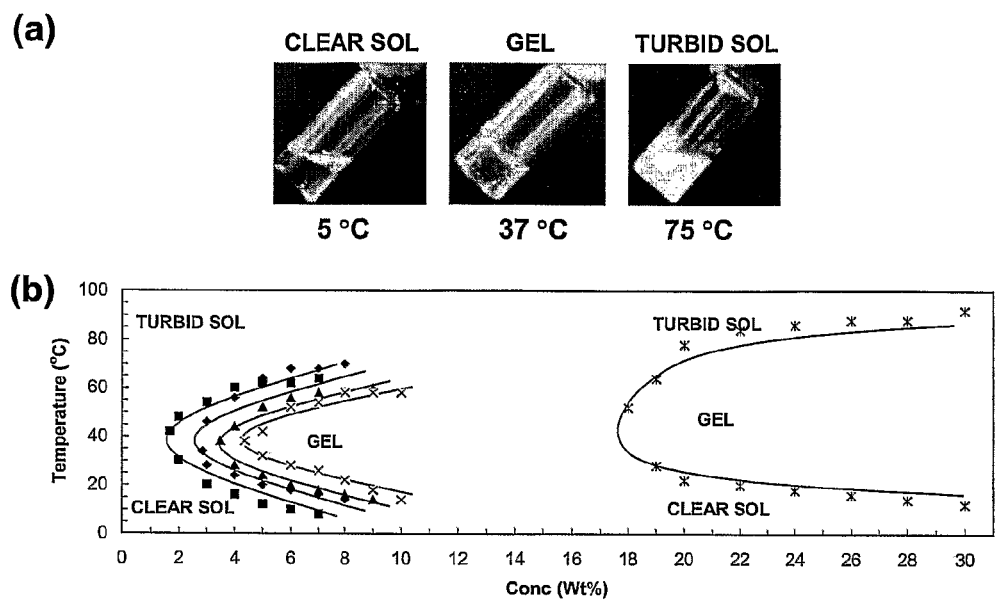
FIG. 9 (a) Graphics showing the gel transition of poly (PHB/PEG/PEG urethane)s (EPH2: 5 wt % in H$_2$O) with increasing temperature. The transition from a clear sol to a gel to a turbid sol is observed in the graphics. (b) Sol-gel phase diagrams of poly(PHB/PEG/PPG urethane)s in aqueous solutions in comparison with Pluronic F127 (▲: EPH1, ■: EPH2, ♦: EPH3 x: EPH5 *: Pluronic F127)

The phase diagrams of the poly(ester urethane)s in aqueous solutions were determined by the test tube inverting method (22a,29). The results are shown in FIG. 9. Three regions can be identified from the diagram, the lower soluble region, gel region and the upper soluble region. As the temperature increased monotonically from 4 to 80° C., the aqueous polymer solution underwent a sol-gel-sol transition. The critical gelation concentration is defined as the minimum copolymer concentration required in aqueous solution before the gelation behavior could be observed. The critical gelation concentrations of the copolymers in this work were found to be between 2-5 wt %. These values are much lower that that reported for many thermogelling copolymers (19-22, 28-30, 32, 37). Examining the gelation properties of the EPH series of copolymers, it appears that the incorporation of a small amount of PHB led to a decrease in the critical gelation concentration (EPH1→EPH2). However, upon further addition of PHB, the critical gelation concentration increased (EPH2→EPH3).

Figure 10:
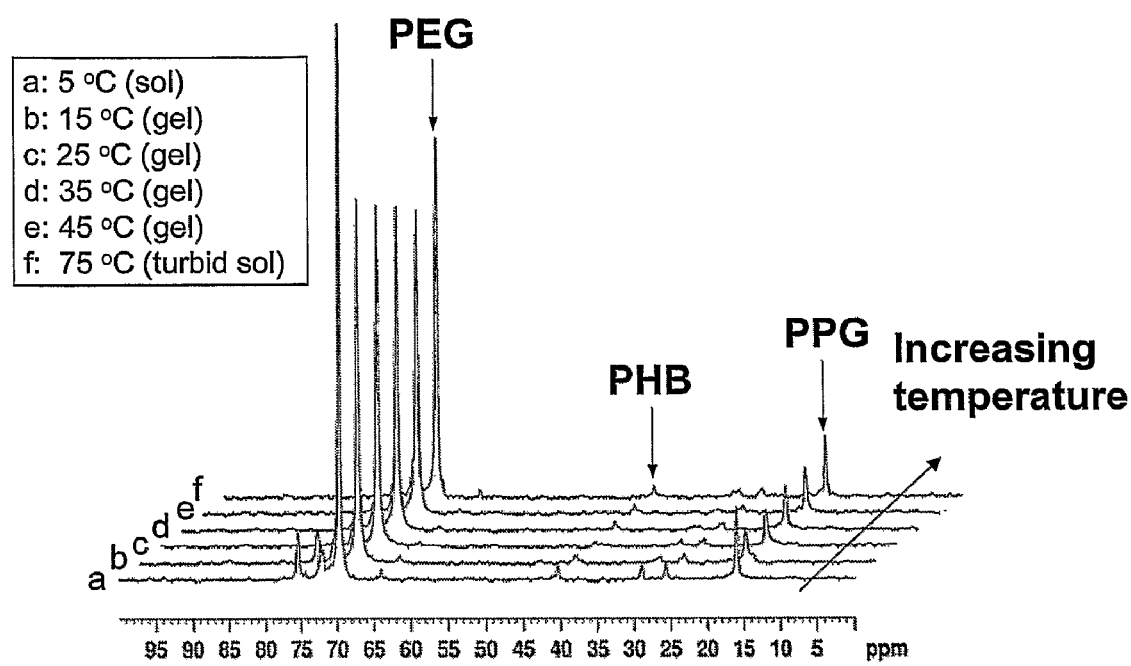
FIG. 10 is $^{13}$C NMR of EPH2 in D$_2$O (5 wt %) at different temperatures.

The molecular environment changes occurring in the sol-gel transition of a 5 wt % gel solution in D$_2$O was monitored by $^{13}$C NMR technique at different temperatures (FIG. 10). In the soluble state, the peaks ascribed to the PEG, PPG and the PHB segments were sharp and well defined as the segments interacted freely with the solvent molecules in the aqueous environment. At temperatures corresponding to the gel state, these peaks were collapsed and broadened. This phenomena has been attributed to the lower dynamic motion of these copolymer segments in the gel state (22a, 28, 29, 31-33, 35). Upon further increase in the temperature, the turbid sol state was obtained and the peaks were consequently seen as sharp and well defined again. This reflects an increase in molecular motion, disruption of the core-corona structure and an exposure of the hydrophobic core to the aqueous environment (31, 35). It has been reported that PEG dissolved in aqueous solution becomes dehydrated at higher temperatures (36). At the turbid sol transition state, there could be significant dehydration of the PEG segments, leading to a phase separation between the polymer and water. This disrupts the core-corona structure and consequently the hydrophobic core is exposed to the aqueous environment (32). In the gel state, the PEG, PPG and PHB peaks were broadened and collapsed as compared with the peaks observed in the sol state. This could be due to the network-like packing of the multiblock polymer chains, with the motion of all the components in the copolymer becoming restricted to a certain extent. This technique studies the sol-gel transition at the molecular level and offers insights on the packing mechanism for the gel formation process.

The viscosities of the hydrogels were studied as a function of temperature. In general, the transition temperature corresponded well with the transition temperature determined using the test tube inverting method. As shown in FIG. 11, as the concentration of EPH2 in aqueous solution increased, the viscosity of the gel increased. It is interesting to note that at the critical gelation concentration of EPH2 (2 wt %), the hydrogel displayed a higher maximum viscosity (43,000 cP) than a hydrogel that is comprised of 20 wt % Pluronics F127 (33,000 cP). This result clearly shows that the gels of this work are studier than that of the Pluronics F127 gels. Above 3 wt %, the EPH2 gels attained a maximum viscosity of more than 55000 cP.

Release of Loaded Protein.

Figure 12:
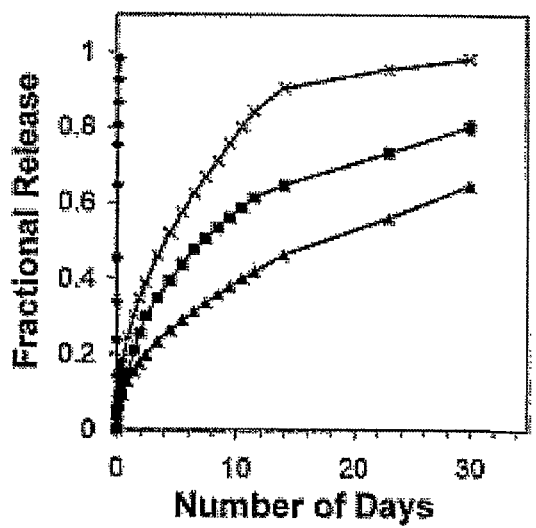
FIG. 12 is BSA protein release profiles from the polymer hydrogels according to embodiments of the invention in comparison with the Pluronic F127 hydrogel.

The increased viscosity of the gels allowed long term sustained release of the model protein, BSA. Preliminary studies showed that sustained release of up to 70 days was achievable with our system. The in vitro release kinetics of the model protein BSA released from the new copolymer hydrogels was studied and compared with Pluronics F127 hydrogel (FIG. 12). Pluronic F127 gel released its entire content of BSA within 4 hours but the gels formed by the new copolymers were able to achieve a sustained release of at least 30 days. The results also demonstrate that tunable release profiles could be obtained by adjusting the composition of the copolymers.

Proposed Sol-Gel Transition Mechanism.

Without being limited to any particular theory, based on the collated results of the micellar and gelation studies we can propose a sol-gel transition mechanism for this multiblock copolymer system as follows. The amphiphilic block copolymers form associated micelles at concentrations in the region of 0.1 wt %. These micelles comprise the hydrophobic PPG and PHB core and the hydrophilic PEG corona that interacts with the water molecules. Upon increasing the concentration to about 2 wt %, the solution is thermoresponsive, existing as solutions at low temperatures and forming gels at elevated temperatures. From a solution state at low temperatures, a monotonic increase in temperature causes the PEG segments to become slightly dehydrated. This provides the driving force for the micellar aggregation as the hydrophobicity and hydrophilicity of the system achieves a balanced state. The PEG corona would self-associate instead of interacting with the neighboring water molecules, forming micelle aggregates. As the micelle aggregates form a close packed structure, a gel state is observed. Further increase in temperature leads to a significant dehydration and the eventual collapse of the PEG corona. This results in the disruption of the core-corona structure and exposes the hydrophobic core to the aqueous environment. This leads to the formation of a soluble turbid state observed at high temperatures.

These multiblock copolymer gels possess lower CMCs and CGCs than the widely studied thermogelling copolymers of the triblock architecture. This could be in part due to the increased association of the micelles brought about by the multiple segments that link the micelles together in a network-like structure. These segmental links facilitate the micellar aggregation process by reducing the degree of freedom possessed by the individual micelles. Cohn et al. developed a series of PEG/PPG/PCL multiblock copolymers which showed higher CGCs as compared with PEG/PPG multiblock copolymers (21). This was attributed to the spatial effect of the caprolactone segments, which affects the packing of the polymer chains. In this work, we observed that the CGC value of the copolymer is dependent on the amount of PHB incorporated into the copolymer. Comparing EPH1 and EPH2, at very low PHB levels, the effect of the spatial hindrances due to the PHB segments were superseded by the strong hydrophobic interaction between the PHB segments. However, a further increase in the PHB content increased the CGC of the copolymer, EPH3, reflecting the spatial effect of the PHB segment on the packing of the polymer chains. (FIG. 9) Comparing the CGC values of EPH3 and EPH5 (3 wt % and 6 wt %, respectively), copolymers of similar PHB content but having different PHB block lengths, it appears that longer PHB segments would lead to a greater spatial hindrance and thus lead to a higher CGC value. This shows that the block length and the content of PHB incorporated into the copolymer could be utilized as parameters in the control of the properties of the thermogelling polymers.

Example 2

Cell Cultivation

L929 mouse fibroblasts were obtained from ATCC and cultivated in DMEM containing 10% fetal bovine serum (FBS) and 1% penicillin/streptomycin. Cells grow as a monolayer and were passaged upon confluence using trypsin (0.5% w/v in PBS). L929 cells were harvested from culture by incubating in trypsin solution for 15 min. The cells were centrifuged and the supernatent was discarded. 3 mL of serum-supplemented DMEM was added to neutralize any residual trypsin. The cells were resuspended in serum-supplemented DMEM at a concentration of $2 \times 10^4$ cells 1 mL. Cells were cultivated at 37° C. and 5% $CO_2$.

Growth on Gel Surface.

EPH copolymers (5 wt %) and F127 copolymers (20 wt %) were dissolved in DMEM. 0.5 mL of the polymer solution was transferred to each well in a 24-well cell culture plate and allowed to incubate at 37° C. for 1 hr. 0.5 mL of the suspended cell solution was added to each well ($10^4$ cells/well). The cell culture plate was allowed to incubate for 3 days. Cells were observed using an inverted microscope (Olympus) (magnification=200×) at time intervals of 1, 2 and 3 days.

Figure 13:
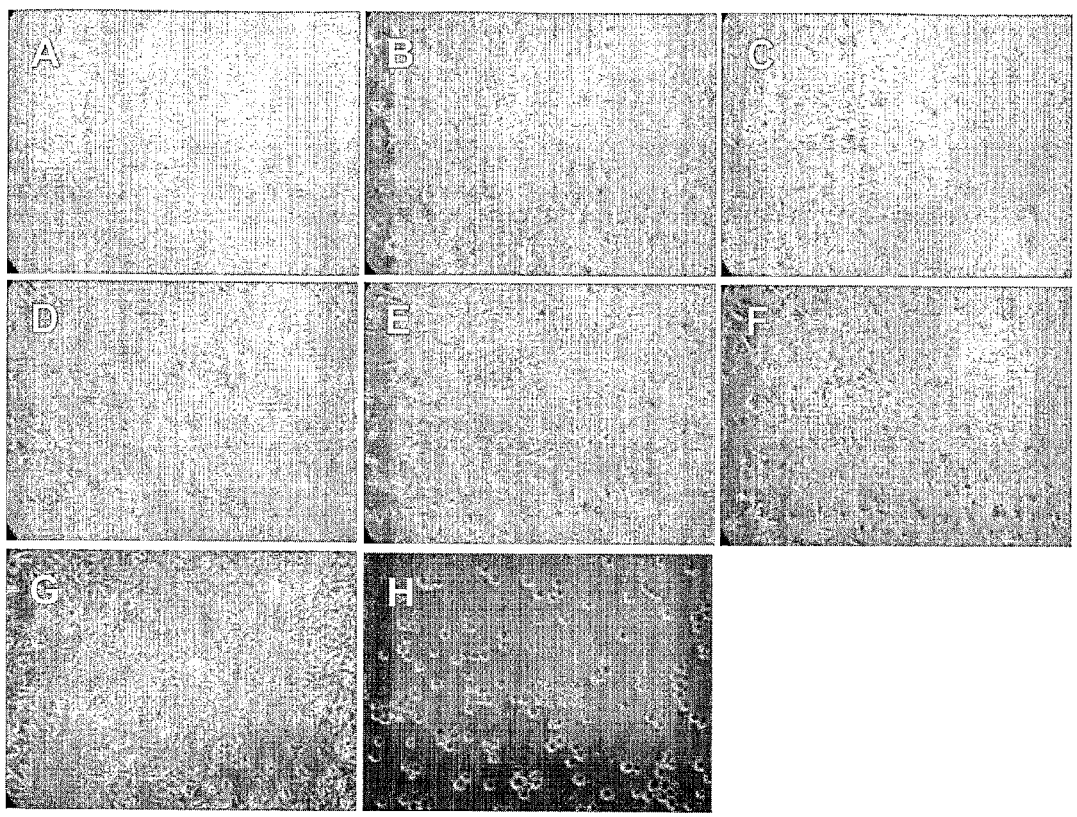
FIG. 13 is photographs of growth of L929 cells on the surface of F127 gel surface [A: 20 wt % B: 15 wt % C: 10 wt % D: 5 wt % E: 2.5 wt % F: 1.25 wt % G: Growth on cell culture dish H: Phenol (0.1 wt %)]
Figure 14:
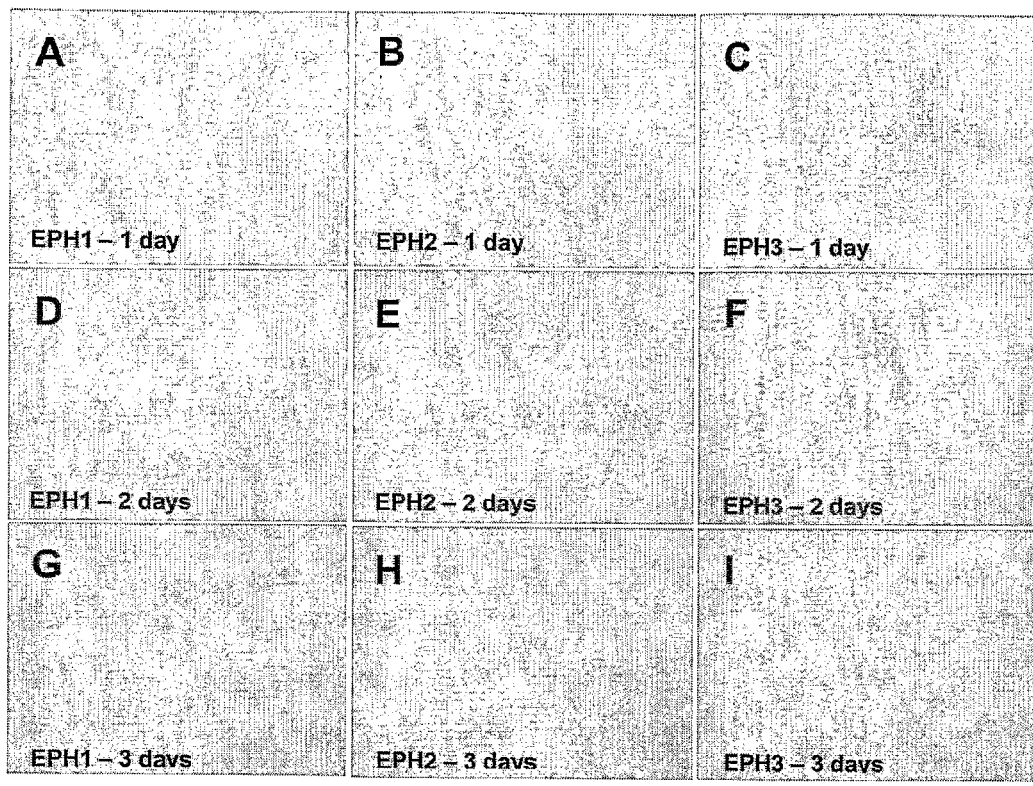
FIG. 14 is photographs of growth of L929 cells on the surface of EPH gels at different incubation days.

Results are shown in FIGS. 13 (F127) and 14 (EPH polymers).

Cell Cultivation.

L929 mouse fibroblasts were cultivated and harvested as previously described. The cells were resuspended in serum-supplemented DMEM at a concentration of $3 \times 10^4$ cells/mL.

In Vitro Cell Viability Direct Method.

To compare the biocompatibility of EPH copolymers and F127 copolymers, in vitro cytotoxicity tests were performed by MTT assay in a 96-well cell culture plate. EPH copolymers and F127 copolymers were dissolved in DMEM (maximum concentration: 100 mg/mL). Cells were seeded at a density of $3 \times 10^3$ cells/well. Phenol was used as a cytotoxic control. Cells not exposed to any biomaterials were used as a positive control. The plates were incubated at 37° C. in a humidified 5% $CO_2$ atmosphere. After 3 days, 10 µl, of 3-(4, 5-dimethylthiazol-2-yl)-2,5-diphenyl tetrazolium bromide (MTT) solution (5 mg/mL) were added to each well. After 4 h of incubation at 37° C., the MTT solution was removed and the insoluble formazan crystals that formed were dissolved in 100 µL of dimethylsulfoxide (DMSO). The absorbance of the formazan product was measured at 570 nm using a spectrophotometer (TECAN SpectrofluorPlus).

Figure 15:
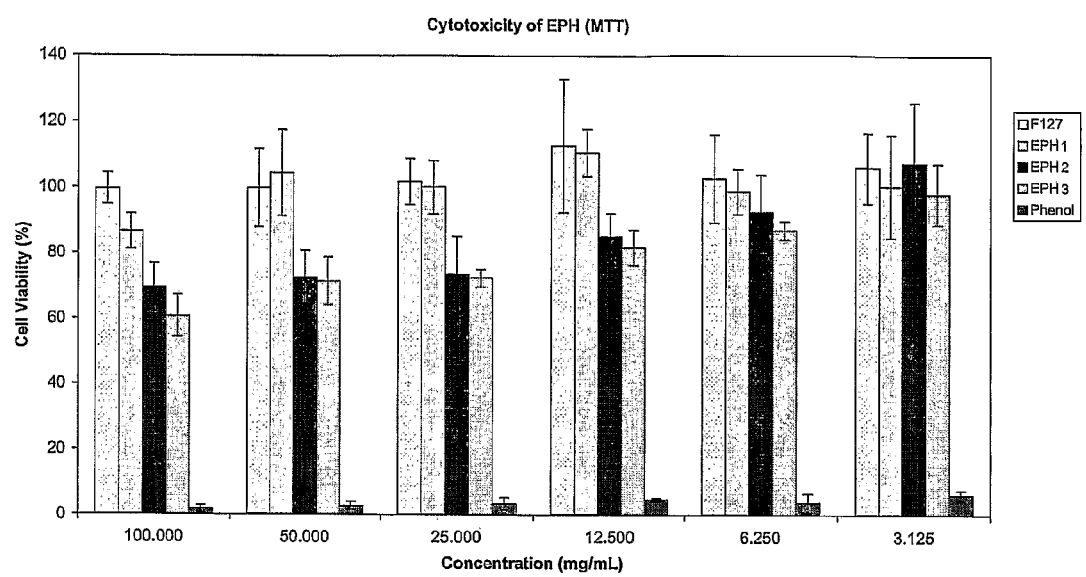
FIG. 15 is a graph depicting cytotoxicity testing results of different concentrations of EPH and F127 polymer by MTT Assay.

Results are shown in FIG. 15.

Obtaining Leachable Products.

1 mL of polymer gels were placed in a cellulose bag and kept in 50 mL of 1×PBS buffer solution at 37° C. in a shaking water bath at 50 rpm. 2 mL of the gel extracts were collected at various time intervals of 1, 3, 7, 14 and 30 days. The solutions were lyophilized and an equivalent amount of DMEM solution was added to re-dissolve the residue.

Testing Leachable Products.

The biocompatibility of leachable gel products of EPH copolymers and F127 copolymers were evaluated by MTT assay. Cells were seeded at a density of $3 \times 10^3$ cells/well. 100 µL of the extract solution in DMEM was added to each well. Phenol was used as a cytotoxic control. Cells not exposed to any biomaterials were used as a positive control. The plates were incubated at 37° C. in a humidified 5% $CO_2$ atmosphere. After 3 days, 10 µL of 3-(4,5-dimethylthiazol-2-yl)-2,5-diphenyl tetrazolium bromide (MTT) solution were added to each well. After 4 h of incubation at 37° C., the solution in the wells were removed and the insoluble formazan crystals that formed were dissolved in 100 µL of dimethylsulfoxide (DMSO). The absorbance of the formazan product was measured at 570 nm using a spectrophotometer (TECAN SpectrofluorPlus).

Figure 16:
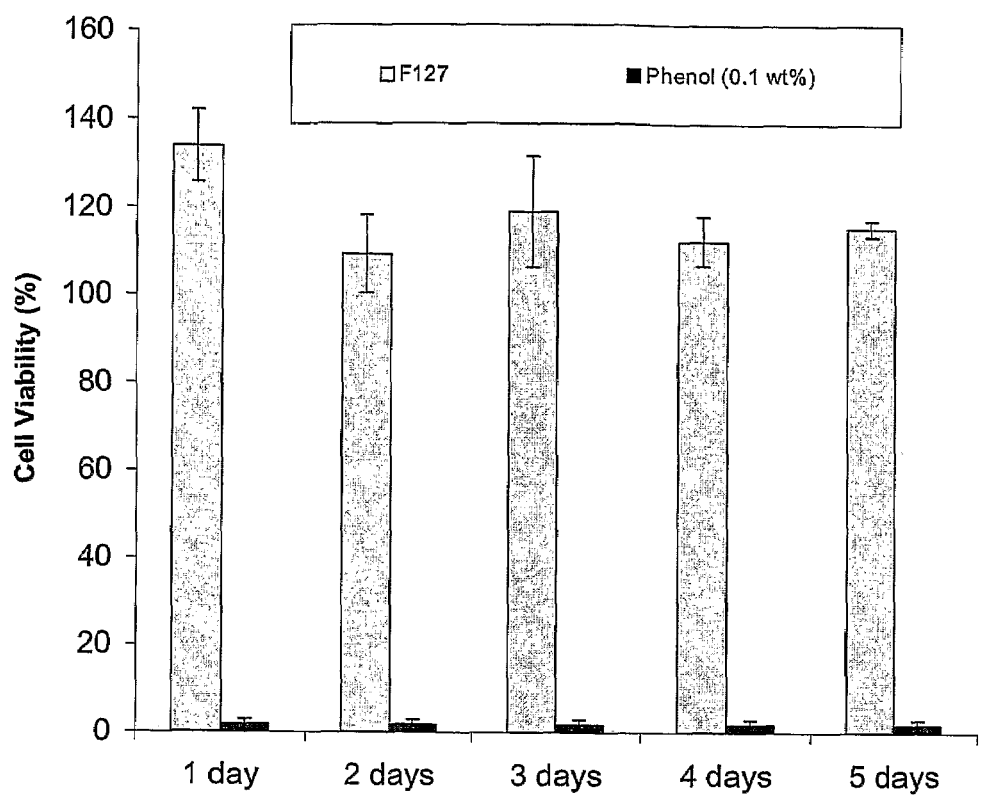
FIG. 16 is a graph depicting cytotoxicity testing of F127 gel release products obtained at different time periods by MTT assay.
Figure 17:
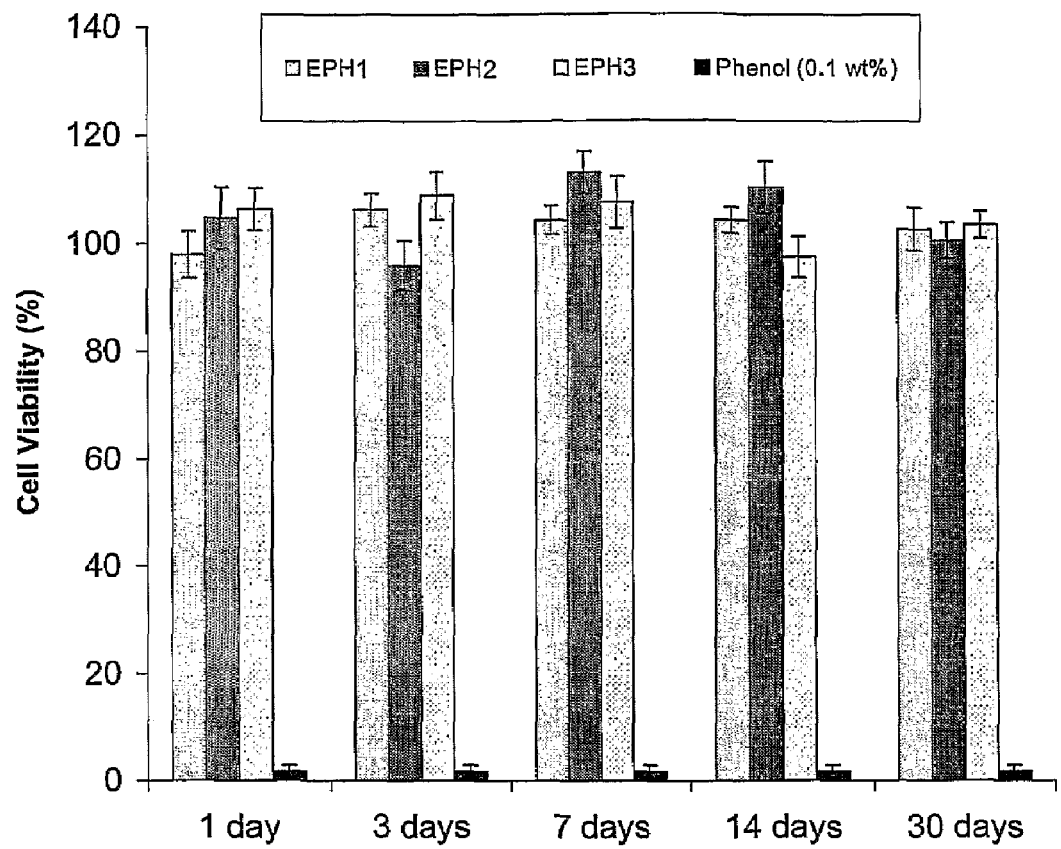
FIG. 17 is a graph depicting cytotoxicity testing of EPH gel release products obtained at different time periods by MTT assay.

Results are shown in FIGS. 16 (F127) and 17 (EPH polymers).

As can be understood by one skilled in the art, many modifications to the exemplary embodiments described herein are possible. The invention, rather, is intended to encompass all such modification within its scope, as defined by the claims.

All documents referred to herein are fully incorporated by reference.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. All technical and scientific terms used herein have the same meaning as commonly understood by one of ordinary skill in the art of this invention, unless defined otherwise.

REFERENCES (1) Huang, K.; Lee, B. P.; Ingram, D. R.; Messersmith, P. B.; *Biomacromolecules* 2002, 3, 397-406.
(2) Daga, A.; Muraglia, A.; Quarto, R.; Cancedda, R.; Corte, G. *Gene Ther.* 2002, 9, 915-921.
(3) Packhaeuser, C. B.; Schnieders, J.; Oster, C. G.; Kissel, T. *Eur. J. Pharm. Biopharm.* 2004, 58, 445-455.
(4) Heller, J.; Barr, J.; Ng, S. Y.; Shen, H. R.; Abdellaoui, S.; Gurny, R.; Castioni, N. V.; Loup, P. J.; Baehni, P.; Mombelli, A. *Biomaterials* 1999, 23, 4397-4404.
(5) Hill-West, J. L.; Chowdhury, S. M.; Slepian, M. J.; Hubbell, J. A. *Proc. Natl. Acad. Sci. U.S.A.* 1994, 91, 5967-5971.
(6) Yokoyama, M. *Crit. Rev. Ther. Drug Carrier Systems* 1992, 9, 213-248.
(7) Gilbert, J. C.; Hadgraft, J.; Bye, A.; Brookes, L. *Int. J. Pharm.* 1986, 32, 223-228.
(8) Nalbandian, R. M.; Henry, R. L.; Wilks, H. S. *J. Biomed. Mater. Res.* 1972, 6, 583-590.
(9) Exner, A. A.; Krupka, T. Y.; Scherrer, K.; Teets, J. M. *J. Control Release* 2005, 106, 188-197.

(10) Esposito, E.; Carotta, Y.; Scabbia, A.; Trombelli, L.; D'Antona, P.; Menegatti, E.; Nastruzzi, C. *Int. J. Pharm.* 1996, 142, 9-23.
(11) Katakam, M.; Ravis, W. R.; Golden, D. L.; Banga, A. K. *Int. J. Pharm.* 1997, 152, 53-58.
(12) Blonder, J. M.; Baird, L.; Fulfs, J.; Rosenthal, G. J. *Life Sci.* 1999, 65, 261-266.
(13) Wout, Z. G. M.; Pec, E. A.; Maggiore, J. A.; Williams, R. H.; Palicharla, P.; Johnston, T. P. *J. Parenteral Sci. & Tech.* 1992, 46, 192-200.
(14) Palmer, W. K.; Emeson, E. E.; Johnston, T. P. *Atherosclerosis* 1998, 136, 115-123.
(15) Ho, A. K.; Bromberg, L.; Huibers, P. D. T.; O'Connor, A. J.; Perera, J. M.; Stevens, G. W.; Hatton, T. A. *Langmuir* 2002, 18, 3005-3013.
(16) Cleary, J.; Bromberg, L.; Magner. E. *Langmuir* 2002, 19, 9162-9172.
(17) Bromberg. L. *Ind. Eng. Chem. Res.* 1998, 37, 4267-4274.
(18) Bromberg. L. *J. Phys. Chem. B.* 1998, 102, 10736-10744.
(19) Ahn, J. S.; Suh, J. M.; Lee, M.; Jeong, B. *Polym. Int.* 2005, 54, 842-847.
(20) Cohn, D.; Sosnik, A.; Levy. A. *Biomaterials* 2003, 24, 3707-3714.
(21) Cohn, D.; Sosnik, A. *Biomaterials* 2005, 26, 349-357.
(22) (a) Hwang, M. J.; Suh, J. M.; Bae, Y. H.; Kim, S. W.; Jeong, B. *Biomacromolecules* 2005, 6, 885-890. (b) Jeong, B.; Bae, Y. H.; Kim, S. W. *J. Controlled Release* 2000, 63, 155-163. (c) Jeong, B.; Bae, Y. H.; Lee, D. S.; Kim, S. W. *Nature* 1997, 388. 860-862.
(23) (a) Li, J.; Li, X.; Ni, X. P.; Leong, K. W. *Macromolecules* 2003, 36, 2661-2667. (b) Li, J.; Ni, X. P.; Li, X.; Tan, N. K.; Lim, C. T.; Ramakrishna, S; Leong, K. W. *Lamgmuir* 2005, 21, 8681-8685. (c) Li, X.; Mya, K. Y.; Ni, X. P.; He, C.; Leong, K. W. *J. Phys. Chem. B* 2006, 110, 5920-5926.
(24) Li, X.; Loh, X. J; Wang, K.; He, C.; Li, J. *Biomacromolecules* 2005, 6, 2740-2747.
(25) Loh, X. J.; Tan, K. K.; Li, X.; Li, J. *Biomaterials* 2006, 27, 1841-1850.
(26) Loh, X. J.; Wang, X.; Li, H.; Li, X.; Li, J. *Materials Science and Engineering C*. in press.
(27) Alexandridis, P.; Holzwarth, J. F.; Hatton, T. A. *Macromolecules* 1994, 27, 2414-2425.
(28) Bae, S. J.; Suh, J. M.; Sohn, Y. S.; Bae, Y. H.; Kim, S. W.; Jeong, B. *Macromolecules* 2005, 38, 5260-5265.
(29) Jeong, B.; Bae, Y. H.; Kim, S. W. *Macromolecules* 1999, 32, 7064-7069.
(30) Behravesh, E.; Shung, A. K.; Jo, S.; Mikos, A. G. *Biomacromolecules* 2002, 3, 153-158.
(31) Jeong, B.; Bae, Y. H.; Kim, S. W. *Colloids and Surfaces B: Biointerfaces* 1999, 16, 185-193.
(32) Jeong, B.; Windisch, Jr., C. F.; Park, M. J.; Sohn, M. J.; Gutowska, A.; Char, K. *J. Phys. Chem. B* 2003, 107, 10032-10039.
(33) Lee, B. H.; Lee, Y. M.; Sohn, Y. S.; Song, S. C. *Macromolecules* 2002, 35, 3876-3879.
(34) Durand, A.; Hourdet, D.; Lafuma, F. *J. Phys. Chem. B* 2000, 104, 9371-9377.
(35) Jeong, B.; Kibbey, M. R.; Birnbaum, J. C.; Won, Y. Y.; Gutowska, A. *Macromolecules* 2000, 33, 8317-8322.
(36) Harris, J. M. *Poly(ethylene glycol) Chemistry*; Plenum Press: New York, 1993; pp 263-268.
(37) Booth, C.; Attwood, D. *Macromol. Rapid. Comm.* 2000, 21, 501-527.

What is claimed is:

1. A polymer consisting of one or more poly(ethylene glycol) blocks, one or more poly(propylene glycol) blocks and one or more poly(hydroxybutyrate) blocks, each block being linked to an adjacent block by a monomer that links adjacent blocks by urethane linkages, the molar ratio of poly(ethylene glycol) to poly(propylene glycol) to poly(hydroxybutyrate) being in the range of about 0.1-10:1:0.01-1 PEG:PPG:PHB.

2. The polymer according to claim 1 wherein the blocks are randomly arranged in the polymer.

3. The polymer according to claim 1 wherein the monomer comprises an alkylene group.

4. The polymer according to claim 3 wherein the alkylene group is a hexamethylene group.

5. The polymer according to claim 1 wherein the at least one poly(ethylene glycol) block has a number average molecular weight of about 10 000 g.mol$^{-1}$ or less.

6. The polymer according to claim 1 comprising about 65 wt % or less of poly(ethylene glycol).

7. The polymer according to claim 1 wherein the at least one poly(propylene glycol) block has a number average molecular weight of about 10 000 g.mol$^{-1}$ or less.

8. The polymer according to claim 1 comprising about 40 wt % or less of poly(propylene glycol).

9. The polymer according to claim 1 wherein the at least one poly(hydroxybutyrate) block has a number average molecular weight of about 10 000 g.mol$^{-1}$ or less.

10. The polymer according to claim 1 comprising about 10 wt % or less of poly(hydroxybutyrate).

11. The polymer according to claim 1 wherein the molar ratio of poly(ethylene glycol) to poly(propylene glycol) is from about 1:1 to about 3:1.

12. The polymer according to claim 1 having a number average molecular weight of about 60 000 g.mol$^{-1}$ or less.

13. The polymer according to claim 1 having a critical gelation concentration from about 1 wt % to about 10 wt % in solution.

14. A composition comprising a polymer of claim 1 and a therapeutic agent.

15. The composition according to claim 14 comprising from about 1 wt % to about 20 wt % of the polymer.

16. The composition according to claim 14 that has a critical gelation temperature below 37° C.

17. The composition according to claim 14 wherein the therapeutic agent is a nucleic acid, including DNA, a peptide, a protein, a small molecule, a cell, an antibody, an antigen, a ligand, a hormone, a growth factor, a cell signalling molecule, a cytokine, an enzyme inhibitor, an antibiotic, a chemotherapeutic agent, an anti-inflammatory agent, or an analgesic.

18. A method of making a polymer of claim 1, the method comprising reacting poly(hydroxybutyrate)-diol, poly(ethylene glycol) and polypropylene glycol) with a diisocyanate.

19. The method according to claim 18 wherein the diisocyanate is hexylmethylene diisocyanate.

20. A method of delivering a therapeutic agent to a subject, the method comprising delivering a composition of claim 14 to the body of a subject.

21. The method according to claim 20 wherein the composition is gelled prior to delivering to the body and delivering comprises surgical implantation.

22. The method according to claim 20 wherein the composition is a liquid or a hydrogel prior to delivering to the body and delivering comprises injection.

23. The polymer of claim 1 formulated together with a therapeutic agent.

24. The polymer of claim 23 formulated to compose from about 1 wt % to about 20 wt % polymer in the formulation.

25. The polymer of claim 23 formulated to have a critical gelation temperature below 37° C.

26. The polymer of claim 23 wherein the therapeutic agent is a nucleic acid, a peptide, a protein, a small molecule, a cell, an antibody, an antigen, a ligand, a hormone, a growth factor, a cell signalling molecule, a cytokine, an enzyme inhibitor, an antibiotic, a chemotherapeutic agent, an anti-inflammatory agent, or an analgesic.

* * * * *